(12) United States Patent
Geurtsen et al.

(10) Patent No.: US 12,290,563 B2
(45) Date of Patent: May 6, 2025

(54) PRODUCTION OF E. COLI O18 BIOCONJUGATES

(71) Applicant: Janssen Pharmaceuticals, Inc., Titusville, NJ (US)

(72) Inventors: Jeroen Geurtsen, Vleuten (NL); Marleen Eveline Weerdenburg, Uithoorn (NL); Pieter Jan Burghout, Pijnacker (NL)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 633 days.

(21) Appl. No.: 17/710,116

(22) Filed: Mar. 31, 2022

(65) Prior Publication Data

US 2022/0323576 A1 Oct. 13, 2022

(30) Foreign Application Priority Data

Apr. 1, 2021 (EP) .................................. 21166781

(51) Int. Cl.
| | | |
|---|---|---|
| *A61K 39/385* | (2006.01) | |
| *A61K 39/02* | (2006.01) | |
| *A61K 39/108* | (2006.01) | |
| *A61K 47/64* | (2017.01) | |
| *A61P 31/04* | (2006.01) | |
| *A61P 37/04* | (2006.01) | |
| *C12N 9/10* | (2006.01) | |
| *A61K 39/00* | (2006.01) | |

(52) U.S. Cl.
CPC ........ *A61K 39/385* (2013.01); *A61K 39/0258* (2013.01); *A61K 47/646* (2017.08); *A61P 31/04* (2018.01); *A61P 37/04* (2018.01); *C12N 9/1081* (2013.01); *A61K 2039/55583* (2013.01); *A61K 2039/6087* (2013.01); *A61K 2039/70* (2013.01)

(58) Field of Classification Search
None
See application file for complete search history.

(56) References Cited

U.S. PATENT DOCUMENTS

| | | |
|---|---|---|
| 4,436,727 A | 3/1984 | Ribi |
| 4,866,034 A | 9/1989 | Ribi |
| 4,877,611 A | 10/1989 | Cantrell |
| 4,912,094 A | 3/1990 | Myers |
| 4,987,237 A | 1/1991 | Myers |
| 5,057,540 A | 10/1991 | Kensil |
| 5,191,072 A | 3/1993 | Hasegawa |
| 5,593,969 A | 1/1997 | Kamireddy |
| 5,750,110 A | 5/1998 | Prieels |
| 6,299,884 B1 | 10/2001 | Van Nest |
| 6,451,325 B1 | 9/2002 | Van Nest |
| 6,491,919 B2 | 12/2002 | Crane |
| 6,676,958 B2 | 1/2004 | Gerber |
| 6,759,241 B1 | 7/2004 | Hone |
| 7,357,936 B1 | 4/2008 | Garcon |
| 8,722,064 B2 | 5/2014 | Reed |
| 9,017,698 B2 | 4/2015 | Eldridge |
| 9,149,521 B2 | 10/2015 | Eldridge |
| 9,149,522 B2 | 10/2015 | Eldridge |
| 9,415,097 B2 | 8/2016 | Eldridge |
| 9,415,101 B2 | 8/2016 | Eldridge |
| 9,504,743 B2 | 11/2016 | Eldridge |
| 2010/0310602 A1 | 12/2010 | Reed |
| 2011/0206758 A1 | 8/2011 | Vandepapeliere |
| 2015/0056224 A1 | 2/2015 | Dubensky, Jr. |
| 2016/0244489 A1 | 8/2016 | Masignani et al. |
| 2018/0099038 A1 | 4/2018 | Tennants |

FOREIGN PATENT DOCUMENTS

| | | |
|---|---|---|
| EP | 0399843 | 11/1990 |
| EP | 0671948 | 9/1995 |
| EP | 0761231 | 3/1997 |
| EP | 0971739 | 1/2000 |
| EP | 1126876 | 8/2001 |
| EP | 1194166 | 4/2002 |
| EP | 1385541 | 2/2004 |
| GB | 2220211 | 1/1990 |
| WO | 2001066572 A2 | 9/2001 |
| WO | 2006116423 | 11/2006 |
| WO | 2006119987 | 11/2006 |

(Continued)

OTHER PUBLICATIONS

International Search Report and Written Opinion issued Sep. 23, 2022 in corresponding PCT/IB2022/053013.
Debroy, Chitrita, et al., "Detection of O antigens in *Escherichia coli*," Animal Health Research Reviews, Cabi Publishing, GB, vol. 12, No. 2, pp. 169-185, Dec. 1, 2011.
Faridmoayer, Amirreza, et al., "Functional characterization of bacterial oligossacharyltransferases involved in O-linked protein glycosylation," Journal of Bacertiology, American Society for Microbiology, vol. 189, No. 22, pp. 8088-8090, Sep. 21, 2007.
Altschul et al. "Basic local alignment search tool," J. Mol. Biol. (1990) 215(3):403-410.
Altschul et al., "Gapped BLAST and PSI-BLAST: a new generation of protein database search programs" Nucleic Acids Res. (1997) 25(17):3389-3402.

(Continued)

*Primary Examiner* — Oluwatosin A Ogunbiyi
(74) *Attorney, Agent, or Firm* — Ice Miller LLP

(57) ABSTRACT

The invention pertains to host cells for producing a bioconjugate of an *E. coli* O18 antigen polysaccharide conjugated to a carrier protein. The host cells are characterized in that they comprise modified Wzy O-antigen polymerases with specific combinations of amino acid substitutions in one or more of positions 199, 377 and 395 as compared to the wild type Wzy O-antigen polymerase of SEQ ID NO: 1, which modified Wzy O-antigen polymerases improve the yield and glycosylation pattern of the O18 bioconjugates produced by the host cells. The invention further relates to methods wherein the host cells are used to produce a bioconjugate of an *E. coli* O18 antigen polysaccharide conjugated to a carrier protein, compositions comprising these bioconjugates, including multivalent compositions comprising bioconjugates of additional O antigen polysaccharide-serotypes.

19 Claims, 1 Drawing Sheet

Specification includes a Sequence Listing.

(56) References Cited

FOREIGN PATENT DOCUMENTS

| WO | 2007109812 | 9/2007 |
|---|---|---|
| WO | 2020191082 A1 | 9/2020 |

OTHER PUBLICATIONS

Carter et al., "A structure-function approach to optimizing TLR4 ligands for human vaccines," Clin Transl Immunology (2016) 5(11):e108 (8 pages).

Cross et al., "Safety and immunogenicity of a polyvalent *Escherichia coli* vaccine in human volunteers," J. Infect Dis. (1994) 170(4):834-840.

Gregg et al., "Rationally Designed TLR4 Ligands for Vaccine Adjuvant Discovery," (2017) 8(3):e00492-00517.

Ho et al., "Preclinical laboratory evaluation of a bivalent *Staphylococcus aureus* saccharide-exotoxin A protein conjugate vaccine," Hum Vaccin (2006) 2(3):89-98.

Lukac et al., "Toxoid of Pseudomonas aeruginosa exotoxin A generated by deletion of an active-site residue," Infect Immun (1988) 56(12):3095-3098.

Poolman et al., "Extraintestinal Pathogenic *Escherichia coli*, a Common Human Pathogen: Challenges for Vaccine Development and Progress in the Field" J. Infect Dis (2016) 213(1):6-13.

Raetz et al., "Bacterial endotoxins: extraordinary lipids that activate eucaryotic signal transduction," J. Bacteriology (1993) 175(18):5745-5753.

Raetz et al., "Lipopolysaccharide endotoxins," Annu Rev Biochem. (2002) 71:635-700.

Reed et al., "Key roles of adjuvants in modern vaccines," Nature Med (2013) 19(12):1597-1608.

Reed et al., "The science of vaccine adjuvants: advances in TLR4 ligand adjuvants," Curr Opin Immunol (2016) 41:85-90.

Stoute et al., "A preliminary evaluation of a recombinant circumsporozoite protein vaccine against Plasmodium falciparum malaria. RTS,S Malaria Vaccine Evaluation Group," (1997) 336(2):86-91.

Wacker et al., "N-Linked Glycosylation in Campylobacter jejuni and Its Functional Transfer into *E. coli*," 298 (5599):1790-1793.

Wacker et al., "Substrate specificity of bacterial oligosaccharyltransferase suggests a common transfer mechanism for the bacterial and eukaryotic systems," Proc. Nat. Acad. Sci. (2006) 103(18):7088-7093.

Woodward et al., "In vitro bacterial polysaccharide biosynthesis: defining the functions of Wzy and Wzz," Nat Chem Biol. (2010) 6(6): 418-423.

European Search Report issued Dec. 14, 2021 in European Patent Application No. 21166781.1.

Anonymous: "O18ab/O18ac family O-antigen polymerase [*Escherichia coli*]—Protein—NCBI", UniParc—JPI000E210611, Jul. 10, 2019 pp. 1-1, XP055838858, Retrieved from the Internet: URL:https://www.ncbi.nlm.nih.gov/protein/WP_115766377 [retrieved Sep. 7, 2021].

Francesca Micoli, et al., "Glycoconjugate vaccines: current approaches towards faster vaccine design," Expert Review of Vaccines, vol. 18, No. 9, pp. 881-895, Aug. 31, 2019.

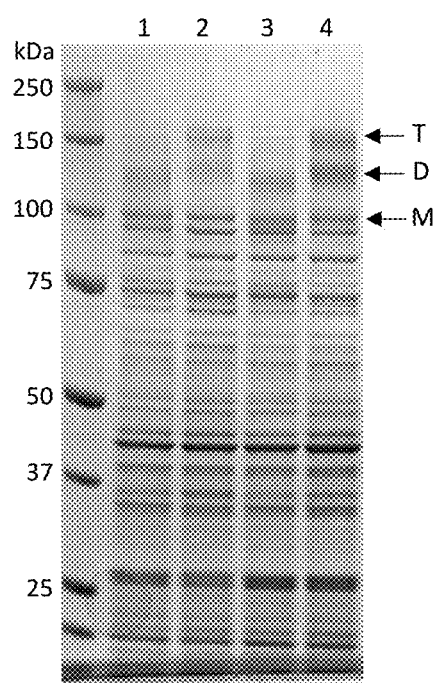

PRODUCTION OF *E. COLI* O18 BIOCONJUGATES

CROSS-REFERENCE TO RELATED APPLICATION

The present application claims priority to EP Application Serial No. 21166781.1, entitled "Production of *E. coli* O18 bioconjugates" filed on Apr. 1, 2021, the disclosure of which is incorporated by reference herein in its entirety.

REFERENCE TO SEQUENCE LISTING SUBMITTED ELECTRONICALLY

This application contains a sequence listing, which is submitted electronically via EFS-Web as an ASCII formatted sequence listing with a file name "SequenceListing126US1" and a creation date of Mar. 28, 2022 and having a size of 34.0 kb. The sequence listing submitted via EFS-Web is part of the specification and is herein incorporated by reference in its entirety.

FIELD OF THE INVENTION

This invention relates to the fields of medical microbiology, immunology and vaccines. In particular the invention relates to host cells comprising improved Wzy O-antigen polymerases for producing bioconjugates of *E. coli* O18 antigen polysaccharide with an increased yield and increased degree of glycosylation. The invention further relates to compositions comprising the bioconjugates of the invention and to the use of such compositions for inducing an immune response against *E. coli* for the prevention or treatment of *E. coli* infections, in particular infections with invasive extra-intestinal pathogenic *E. coli* (ExPEC) disease.

BACKGROUND OF THE INVENTION

Extraintestinal pathogenic *Escherichia coli* (ExPEC) strains are normally harmless inhabitants of the human gastrointestinal tract, alongside commensal *E. coli* strains. ExPEC isolates cannot readily be distinguished from commensal isolates by serotype, although many clonal lineages are dominated by ExPEC, as defined by O-antigen, capsule and flagellar antigen serotypes (abbreviated as O:K:H, for example O25:K1:H4). In contrast to commensal *E. coli*, ExPEC strains express a broad array of virulence factors enabling them to colonize the gastrointestinal tract, as well as to cause a wide range of extraintestinal infections, which are associated with a significant healthcare cost burden due to hospitalization and death. Neonates, the elderly, and immunocompromised patients are particularly susceptible to ExPEC infection, including invasive ExPEC disease (IED).

The O-antigen comprises the immunodominant component of the cell wall lipopolysaccharide (LPS) in Gram-negative bacteria, including *E. coli*. There are currently >180 serologically unique *E. coli* O-antigens identified, with the vast majority of ExPEC isolates classified within less than 20 O-antigen serotypes. Full-length *E. coli* O-antigens are typically comprised of about 10 to 25 repeating sugar units attached to the highly conserved LPS core structure, with each component synthesized separately by enzymes encoded predominantly in the rfb and rfa gene clusters, respectively. Following polymerization of the O-antigen, the O-antigen polysaccharide backbone may be modified, typically through the addition of acetyl or glucose residues. These modifications effectively increase serotype diversity by creating antigenically distinct serotypes that share a common polysaccharide backbone, but differ in side branches. Genes encoding O-antigen modifying enzymes typically reside outside of the rfb cluster on the chromosome, and in some cases, these genes are found within lysogenic bacteriophages.

Efforts toward the development of a vaccine to prevent ExPEC infections have focused on O-antigen polysaccharide conjugates. A 12-valent O-antigen conjugate vaccine was synthesized through extraction and purification of O-antigen polysaccharide and chemical conjugation to detoxified *Pseudomonas aeruginosa* exotoxin A and tested for safety and immunogenicity in a Phase 1 clinical study (Cross et al., J. Infect. Dis. (1994) v. 170, pp. 834-40). This candidate vaccine was never licensed for clinical use. A bioconjugation system in *E. coli* has been developed recently, in which the antigen polysaccharide and the carrier protein are both synthesized in vivo and subsequently conjugated in vivo through the activities of the oligosaccharyl transferase PglB, a *Campylobacter jejuni* enzyme, expressed in *E. coli* (Wacker et al., Proc. Nat. Acad. Sci. (2006) v. 103, pp. 7088-93). This N-linked protein glycosylation system is capable of the transfer of diverse polysaccharides to a carrier protein, allowing for methods to purify the bioconjugate from bacteria wherein it is expressed. Bioconjugation has been used successfully to produce conjugate polysaccharide for an *E. coli* four-valent O-antigen candidate vaccine (Poolman and Wacker, J. Infect. Dis. (2016) v. 213(1), pp. 6-13; WO 2015/124769; WO 2017/035181).

A composition comprising 10 bioconjugates (O1A, O2, O4, O6A, O8, O15, O16, O18A, O25B and O75, the composition being referred to as ExPEC10V) has been described and is in clinical trials (e.g. WO2020/191082A1).

It was observed that the product yield for bioconjugates with O18A antigen polysaccharide was lowest compared to the other nine bioconjugates prepared for ExPEC10V (WO2020/191082A1). Furthermore, the O18A bioconjugate so produced appeared to contain a relatively high amount of glycans made up of a limited number of O18A antigen polysaccharide repeat units, referred to as 'sEPA' (i.e. EPA carrier protein having polysaccharide chains with only about 1-3 repeat units, which amounted to more than 20% of the O18A bioconjugates in the periplasmic fraction in the production process for the O18A bioconjugate drug substance), which sEPA product is not easily separated from the preferred bioconjugate that comprises mainly glycans wherein the O18A antigen polysaccharide is made up of at least five repeat units. ExPEC isolates belonging to the O18 serogroup have been commonly identified in contemporary surveillance studies of U.S. and EU blood isolates, and O18 conjugates are therefore deemed to be a relevant component of an ExPEC vaccine. Improving the yields of conjugates of O18 antigen polysaccharide would therefore be desired.

It is thus an object of the invention to provide for materials and methods for increasing the product yield of bioconjugates comprising O18 antigen polysaccharide during production and/or to produce materials and methods for obtaining O18 bioconjugates with decreased relative amounts of sEPA as compared to O18 bioconjugates obtained using a previously described production process. It is another object of the invention to provide for materials and methods for producing bioconjugates of *E. coli* O18A antigen polysaccharide with an increased degree of glycosylation as compared to O18 bioconjugates obtained using materials and methods as previously described.

SUMMARY OF THE INVENTION

In a first aspect, the invention relates to a gram-negative bacterial host cell comprising: (a) a carrier protein comprising at least one glycosylation consensus sequence; (b) an *E. coli* O18 rfb locus; and, (c) an oligosaccharyltransferase; wherein the cell comprises a polypeptide having Wzy O-antigen polymerase activity, which polypeptide comprises an amino acid sequence with at least 95% identity with SEQ ID NO: 1, wherein the amino acid sequence comprises: i) isoleucine (Ile, I) at a position that corresponds to position 199 in SEQ ID NO: 1, lysine (Lys, K) at a position that corresponds to position 377 in SEQ ID NO: 1 and alanine (Ala, A) at a position that corresponds to position 395 in SEQ ID NO: 1; ii) threonine (Thr, T) at a position that corresponds to position 199 in SEQ ID NO: 1, lysine at a position that corresponds to position 377 in SEQ ID NO: 1 and valine (Val, V) at a position that corresponds to position 395 in SEQ ID NO: 1; iii) threonine at a position that corresponds to position 199 in SEQ ID NO: 1, lysine at a position that corresponds to position 377 in SEQ ID NO: 1 and alanine at a position that corresponds to position 395 in SEQ ID NO: 1; iv) isoleucine at a position that corresponds to position 199 in SEQ ID NO: 1, lysine at a position that corresponds to position 377 in SEQ ID NO: 1 and valine at a position that corresponds to position 395 in SEQ ID NO: 1; or v) isoleucine at a position that corresponds to position 199 in SEQ ID NO: 1, methionine (Met, M) at a position that corresponds to position 377 in SEQ ID NO: 1 and alanine at a position that corresponds to position 395 in SEQ ID NO: 1.

In one embodiment, in the host cell, the polypeptide having Wzy O-antigen polymerase activity comprises the amino acid sequence of SEQ ID NO: 1, except that the amino acid sequence comprises: i) Ile at position 199, Lys at position 377 and Ala at position 395; ii) Thr at position 199, Lys at position 377 and Val at position 395; iii) Thr at position 199, Lys at position 377 and Ala at position 395; iv) Ile at position 199, Lys at position 377 and Val at position 395; or v) Ile at position 199, Met at position 377 and Ala at position 395; wherein all positions are corresponding to those in SEQ ID NO: 1.

In one embodiment, in the host cell, the polypeptide having Wzy O-antigen polymerase activity comprises Ile at position 199, Lys at position 377 and Ala at position 395, wherein the positions correspond to those in SEQ ID NO: 1.

In one embodiment, the host cell comprises a polynucleotide or vector encoding the polypeptide having Wzy O-antigen polymerase activity is integrated into the genome of the host cell.

In one embodiment, the host cell is an *Escherichia coli* host cell. In a preferred embodiment, the host cell is an *E. coli* K-12 strain, more preferably *E. coli* K-12 strain W3110.

In one embodiment, in the host cell, at least one of: a) the oligosaccharyl transferase comprises an amino acid sequence with at least 95% sequence identity to SEQ ID NO: 6; b) the carrier protein comprises SEQ. ID NO: 3; and, c) the *E. coli* O18 rfb locus is an rfb locus of an *E. coli* strain having serotype O18A. Preferably, the oligosaccharyl transferase comprises the amino acid sequence of SEQ ID NO: 6.

In one embodiment, the host cell comprises an *E. coli* O18 rfb locus with a nucleotide sequence encoding a Wzy O-antigen polymerase that encodes a polypeptide having Wzy O-antigen polymerase activity as defined herein above.

In a further aspect, the invention pertains to a method for producing a bioconjugate of an *E. coli* O18 antigen polysaccharide conjugated to a carrier protein, the method comprising: (a) culturing a host cell of the invention as defined herein above, to produce the bioconjugate. Preferably, the method further comprises recovery of the bioconjugate.

In one embodiment, the method further comprises formulating the recovered bioconjugate into a pharmaceutical composition.

In one embodiment, the method further comprises adding one or more additional bioconjugates of *E. coli* O-antigen polysaccharides conjugated to a carrier protein to the pharmaceutical composition to obtain a multivalent bioconjugate composition. Preferably, the one or more additional bioconjugates comprise at least one O-antigen polysaccharide selected from the group consisting of *E. coli* serotypes O1, O2, O4, O6, O8, O15, O16, O25 and O75. In a preferred embodiment, the multivalent bioconjugate composition produced in the method comprises: (i) the bioconjugate of an *E. coli* O18A antigen polysaccharide conjugated to a carrier protein; (ii) a bioconjugate of an *E. coli* O1A antigen polysaccharide conjugated to a carrier protein; (iii) a bioconjugate of an *E. coli* O2 antigen polysaccharide conjugated to a carrier protein; (iv) a bioconjugate of an *E. coli* glucosylated O4 antigen polysaccharide conjugated to a carrier protein; (v) a bioconjugate of an *E. coli* O6A antigen polysaccharide conjugated to a carrier protein; (vi) a bioconjugate of an *E. coli* O15 antigen polysaccharide conjugated to a carrier protein; (vii) a bioconjugate of an *E. coli* O16 antigen polysaccharide conjugated to a carrier protein; (viii) a bioconjugate of an *E. coli* O25B antigen polysaccharide conjugated to a carrier protein; and, (ix) a bioconjugate of an *E. coli* O75 antigen polysaccharide conjugated to a carrier protein, wherein preferably the carrier protein in each bioconjugate comprises SEQ ID NO: 3. In a more preferred embodiment, the multivalent bioconjugate composition produced in the method further comprises: (x) a bioconjugate of an *E. coli* O8 antigen polysaccharide conjugated to a carrier protein, wherein preferably the carrier protein comprises SEQ ID NO: 3.

DESCRIPTION OF THE FIGURE

FIG. 1. Coomassie-stained SDS-PAGE loaded with periplasmic extracts from shake flask cultures of *E. coli* production strain W3110 for O18A bioconjugates containing Wzy variants with SEQ ID NO: 1 (lane 1 and 3) or with amino acid substitutions 199I, 377K, 395A (lane 2 and 4) that were induced for O18A polysaccharide bioconjugate expression. In samples loaded on lanes 1 and 2 the oligosaccharyl transferase enzyme PglB was expressed from a size-reduced expression plasmid whereas in lane 3 and 4 the vector backbone of the PglB expression plasmid contained an additional 4500 bp of DNA sequence, comprising non-coding DNA and the lac repressor gene lacI, which appeared optimal for product expression. Bands showing O18A polysaccharide bioconjugate material are indicated with arrows, depicting the approximate size of mono-glycosylated EPA (M), di-glycosylated EPA (D) and tri-glycosylated EPA (T).

DESCRIPTION OF THE INVENTION

Unless defined otherwise, all technical and scientific terms used herein have the same meaning commonly understood to one of ordinary skill in the art to which this invention pertains. Otherwise, certain terms cited herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Throughout this description and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

The word "about" or "approximately" when used in association with a numerical value means that the value may be the given value plus or minus 20% of the value, preferably plus or minus 10% of the value, more preferably plus or minus 5% of the value.

Sequence identity is herein defined as a relationship between two or more amino acid (polypeptide or protein) sequences or two or more nucleic acid (polynucleotide) sequences, as determined by comparing the sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods.

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithm (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). Most preferably, sequence alignments are performed in a ClustalW (1.83) sequence alignment using default settings.

Alternatively, percentage similarity or identity may be determined by searching against public databases, using algorithms such as FASTA, BLAST, etc. Thus, the nucleic acid and protein sequences of the present invention can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to wzy nucleic acid molecules of the invention. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTx and BLASTn) can be used. See the homepage of the National Center for Biotechnology Information at http://www.ncbi.nlm.nih.gov/.

Unless otherwise indicated, the term "at least" preceding a series of elements is to be understood to refer to every element in the series.

DETAILED DESCRIPTION OF THE INVENTION

The inventors of present application have surprisingly found that the use of a Wzy O-antigen polymerase that differs from the reference sequence at one or more specific positions led to a significant improvement of the production yield of O18 antigen polysaccharide bioconjugate. In addition, the use of such polymerase was found to surprisingly facilitate the production of an O18 antigen polysaccharide conjugate with an increased glycan to protein ratio and/or increased occupancy of glycosylation sites.

Accordingly, in a first aspect, the invention provides a host cell for use in producing a bioconjugate of an E. coli O18 antigen polysaccharide conjugated to a carrier protein.

In one embodiment, a host cell of the invention at least comprises: (a) a carrier protein comprising at least one glycosylation consensus sequence; (b) an E. coli O18 rfb locus; (c) an oligosaccharyltransferase; and, (d) a polypeptide of the invention having Wzy O-antigen polymerase activity.

In the host cell, the polypeptide of the invention having Wzy O-antigen polymerase activity is a polypeptide comprising an amino acid sequence that has at least 90, 91, 92, 93, 94, 95, 96, 97, 98 or 99% amino acid sequence identity with the amino acid sequence of SEQ ID NO: 1, and further having O-antigen polymerase activity. Whether or not a polypeptide of the invention has O-antigen polymerase activity can be assayed by expressing a nucleotide sequence encoding the Wzy O-antigen polymerase in a suitable host cell and determining the amount of polymerized O-antigen produced by methods known to the person skilled in the art or for example as described in Woodward et al. (2010, Nat Chem Biol. 2010 June; 6(6): 418-423), which is herein incorporated in its entirety.

In one embodiment, a host cell of the invention comprises a polypeptide having Wzy O-antigen polymerase activity, which polypeptide comprises an amino acid sequence with at least 90, 91, 92, 93, 94, 95, 96, 97, 98 or 99% identity with SEQ ID NO: 1, wherein the amino acid sequence comprises:

i) isoleucine at a position that corresponds to position 199 in SEQ ID NO: 1, lysine at a position that corresponds to position 377 in SEQ ID NO: 1 and alanine at a position that corresponds to position 395 in SEQ ID NO: 1;

ii) threonine at a position that corresponds to position 199 in SEQ ID NO: 1, lysine at a position that corresponds to position 377 in SEQ ID NO: 1 and valine at a position that corresponds to position 395 in SEQ ID NO: 1;

iii) threonine at a position that corresponds to position 199 in SEQ ID NO: 1, lysine at a position that corresponds to position 377 in SEQ ID NO: 1 and alanine at a position that corresponds to position 395 in SEQ ID NO: 1;

iv) isoleucine at a position that corresponds to position 199 in SEQ ID NO: 1, lysine at a position that corresponds to position 377 in SEQ ID NO: 1 and valine at a position that corresponds to position 395 in SEQ ID NO: 1; or, v) isoleucine at a position that corresponds to position 199 in SEQ ID NO: 1, methionine at a position that corresponds to position 377 in SEQ ID NO: 1 and alanine at a position that corresponds to position 395 in SEQ ID NO: 1.

An amino acid position that corresponds to one of amino acid positions 199, 377 or 395 in SEQ ID NO: 1, respectively, is herein understood to refer to a position in an amino acid sequence other than SEQ ID NO: 1 that aligns with one of the positions 199, 377 or 395 in SEQ ID NO: 1, respectively, in a sequence alignment of SEQ ID NO: 1 with that sequence other than SEQ ID NO: 1, preferably in a ClustalW (1.83) sequence alignment with SEQ ID NO: 1, preferably using default settings. The skilled person will know how to identify corresponding amino acid positions in Wzy O-antigen polymerase amino acid sequences other than SEQ ID NO: 1 using amino acid sequence alignment algorithms as defined herein.

In a preferred embodiment, a host cell of the invention comprises a polypeptide having Wzy O-antigen polymerase activity, which polypeptide comprises the amino acid sequence of SEQ ID NO: 1, except that the amino acid sequence comprises: i) isoleucine at a position that corresponds to position 199 in SEQ ID NO: 1, lysine at a position that corresponds to position 377 in SEQ ID NO: 1, and alanine at a position that corresponds to position 395 in SEQ ID NO: 1; ii) threonine at a position that corresponds to position 199 in SEQ ID NO: 1, lysine at a position that corresponds to position 377 in SEQ ID NO: 1, and valine at a position that corresponds to position 395 in SEQ ID NO: 1; iii) threonine at a position that corresponds to position 199 in SEQ ID NO: 1, lysine at a position that corresponds to position 377 in SEQ ID NO: 1, and alanine at a position that corresponds to position 395 in SEQ ID NO: 1; iv) isoleucine at a position that corresponds to position 199 in SEQ ID NO: 1, lysine at a position that corresponds to position 377 in SEQ ID NO: 1, and valine at a position that corresponds to position 395 in SEQ ID NO: 1; or v) isoleucine at a position that corresponds to position 199 in SEQ ID NO: 1, methionine at a position that corresponds to position 377 in SEQ ID NO: 1, and alanine at a position that corresponds to position 395 in SEQ ID NO: 1. Thus, in this embodiment the host cell of the invention comprises a polypeptide having Wzy O-antigen polymerase activity, which polypeptide comprises the amino acid sequence of SEQ ID NO: 1, except that the amino acid sequence comprises: i) isoleucine at position 199 in SEQ ID NO: 1, lysine at position 377 in SEQ ID NO: 1 and alanine at position 395 in SEQ ID NO: 1; ii) lysine at position 377 in SEQ ID NO: 1; iii) lysine at position 377 in SEQ ID NO: 1 and alanine at position 395 in SEQ ID NO: 1; iv) isoleucine at position 199 in SEQ ID NO: 1 and lysine at position 377 in SEQ ID NO: 1; or, v) isoleucine at position 199 in SEQ ID NO: 1 and alanine at position 395 in SEQ ID NO: 1.

In a particularly preferred embodiment, a host cell of the invention comprises a polypeptide having Wzy O-antigen polymerase activity, which polypeptide comprises, isoleucine at a position that corresponds to position 199 in SEQ ID NO: 1, lysine at a position that corresponds to position 377 in SEQ ID NO: 1, and alanine at a position that corresponds to position 395 in SEQ ID NO: 1.

As will be understood by the skilled person, in one embodiment, for expression of a polypeptide having Wzy O-antigen polymerase activity, a host cell of the invention will preferably comprise a polynucleotide encoding the polypeptide having Wzy O-antigen polymerase activity of the invention as defined herein above. The polynucleotide may be preceded by a promoter operably linked thereto. In certain embodiments, the promoter is endogenous to the Wzy O-antigen polymerase coding sequence. In certain preferred embodiments, the promotor is an endogenous promotor driving the expression of Wzy O-antigen polymerase in a bacterium of the Enterobacteriaceae family, preferably a bacterium of the genus *Escherichia*, more preferably a bacterium of the species *E. coli*. In other embodiments, the promotor is heterologous to the Wzy coding sequence e.g. a strong promotor known to the skilled person for use in recombinant expression systems is used. For example, the promotor is an inducible or constitutive prokaryotic promoter, such an ara, phoA, tac, tet, trc, trp, PBAD, APL, T5, or T7 promoter.

In certain embodiments, the invention provides an isolated polynucleotide that can be used in the construction of a host cell according to the invention. The polynucleotide can be a recombinant, synthetic or artificial polynucleotide. The polynucleotide may be in any form of nucleic acid, e.g. DNA or RNA, preferably DNA. The polynucleotide may comprise one or more nucleotides that are not present in a naturally occurring Wzy encoding polynucleotide, such as the naturally occurring Wzy encoding polynucleotide of SEQ ID NO: 2. Specifically, the polynucleotide for use in the invention will at least differ from a naturally occurring Wzy encoding polynucleotide such as SEQ ID NO: 2 in one or more of the codons corresponding to the positions 199, 377 and 395 in SEQ ID NO: 1. In addition the polynucleotide for use in the invention can differ from a naturally occurring Wzy encoding polynucleotide in codons other than the positions corresponding to at least one of the positions 199, 377 and 395 in SEQ ID NO:1. The polynucleotide may have one or more nucleotides that are not present in a naturally occurring Wzy-encoding polynucleotide at its 5'-end and/or 3'-end. Skilled persons may, using routine techniques, make nucleotide substitutions that do not affect the polypeptide sequence encoded by the polynucleotides described to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence.

As will further be understood by the skilled person, in one embodiment, the polynucleotide encoding the polypeptide having Wzy O-antigen polymerase activity of the invention as defined herein above may be comprised in an expression construct or vector. Preferably in the expression construct the polynucleotide encoding the polypeptide having Wzy O-antigen polymerase activity is operably linked to expression control sequence for expression of the polypeptide in the host cell of the invention, e.g. in an expression cassette. Such expression control sequence can include a promoter as specified above and can further include a Shine-Dalgarno sequence, a transcription termination sequence, etc., etc. In one embodiment, expression construct is comprised in a vector. In one embodiment, the vector is an episomal vector, such as a plasmid or a viral vector, preferably a plasmid. In another embodiment, the polynucleotide, the vector, or the expression construct is integrated into the genome of the host cell. In certain embodiments, the vector or expression construct is preferably in the form of DNA. In certain embodiments, the vector comprises the polynucleotide of the invention operably linked to a promoter, meaning that the polynucleotide is under control of a promoter. In certain embodiments, the polynucleotide encoding the polypeptide having Wzy O-antigen polymerase activity of the invention as defined herein is integrated into its natural position in the rfb locus in the genome of the host cell, for instance created by site-directed mutagenesis, using homologous recombination-based genetic modification techniques, which are known to the person skilled in the art of molecular biology.

The host cell of the invention for use in producing a bioconjugate of an *E. coli* O18 antigen polysaccharide conjugated to a carrier protein, is a bacterial host cell. In one embodiment, the host cell is a gram-negative bacterial host cell. Suitable bacterial or prokaryotic host cells for use in producing a bioconjugate comprising an *E. coli* O18 antigen, include, but are not limited to, *Escherichia* species, *Shigella* species, *Klebsiella* species, *Xhantomonas* species. *Salmonella* species. *Yersinia* species, *Lactococcus* species, *Lactobacillus* species. *Pseudomonas* species, *Corynebacterium* species, *Streptomyces* species. *Streptococcus* species. *Staphylococcus* species. *Bacillus* species, and *Clostridium* species. In a preferred embodiment, the host cell of the invention is an *Escherichia coli* host cell, more preferably an *E. coli* K-12 strain, such as strain W3110, the latter being particularly preferred.

In one embodiment, the host cell is a non-naturally occurring host cell. Thus, the host cell may be derived from a naturally occurring isolate, e.g. a clinical isolate, which has been modified to express a polypeptide having Wzy O-antigen polymerase activity as described herein and, which preferably has been further modified to comprise one or more or all of i) an O18 rfb locus as herein defined, ii) (a nucleic acid construct for expression of) a carrier protein comprising at least one glycosylation consensus sequence as herein defined, and iii) (a nucleic acid construct for expression of) an oligosaccharyl transferase as herein defined.

The host cell of the invention for use in producing a bioconjugate of an *E. coli* O18 antigen polysaccharide conjugated to a carrier protein further preferably comprises an oligosaccharyl transferase (OST) for transfer of oligosaccharides to N-glycosylation sites on the carrier protein. Preferably therefore, a host cell as herein provided comprises a nucleotide sequence encoding an oligosaccharyl transferase (OST). Oligosaccharyl transferases as used herein are enzymes that transfer lipid-linked oligosaccharides to residues of nascent polypeptide chains that comprise a glycosylation consensus motif, for example to asparagine (Asn, N) residues of nascent polypeptide chains that comprise an N-glycosylation consensus motif, examples of such N-glycosylation consensus motifs being SEQ ID NO: 4 or Asn-X-Ser(Thr). Throughout this application it is to be understood that for the N-glycosylation motif Asn-X-Ser (Thr), X can be any amino acid except proline. Preferably such oligosaccharyl transferases transfer the oligosaccharides to asparagine residues of SEQ ID NO: 4 in a polypeptide chain of a carrier protein as described herein. The nucleic acid that encodes an oligosaccharyl transferase can be native to the host cell, or can be introduced into the host cell using genetic approaches. In preferred embodiments, the oligosaccharyl transferase is heterologous to the host cell. *E. coli* does not naturally comprise an oligosaccharyl transferase, and hence if *E. coli* is used as a host cell for production of bioconjugates, a heterologous oligosaccharyl transferase is comprised in such host cell, e.g. upon introduction by genetic engineering. The oligosaccharyl transferase can be from any source known in the art in view of the present disclosure.

In certain preferred embodiments, the oligosaccharyl transferase is an oligosaccharyl transferase from *Campylobacter*. For example, in one embodiment, the oligosaccharyl transferase is an oligosaccharyl transferase from *Campylobacter jejuni* (i.e., PglB; see, e.g., Wacker et al., 2002, Science 298:1790-1793; see also, e.g., NCBI Gene ID: 3231775, UniProt Accession No. O86154). In another embodiment, the oligosaccharyl transferase is an oligosaccharyl transferase from *Campylobacter lari* (see, e.g., NCBI Gene ID: 7410986).

In specific embodiments, the oligosaccharyl transferase is PglB from *Campylobacter jejuni*, including the natural (wild-type) protein or any variant thereof, such as those described in International Patent Application Publications WO 2016/107818 and WO 2016/107819. PglB can transfer lipid-linked oligosaccharides to asparagine residues in the consensus sequences SEQ ID NO: 4 and Asn-X-Ser(Thr). In particular embodiments, the PglB oligosaccharyl transferase is a polypeptide having oligosaccharyl transferase as defined herein, which polypeptide comprises an amino acid sequence with at least 80, 85, 90, 95, 96, 97, 98 or 99% sequence identity to SEQ ID NO: 6. In a preferred embodiment, the PglB oligosaccharyl transferase comprises an amino acid sequence that is identical to SEQ ID NO: 6. In certain embodiments one or more endogenous glycosylation consensus sequences in a wild-type PglB have been mutated to avoid PglB autoglycosylation, e.g. SEQ ID NO: 6 comprising the mutation N534Q. Examples of variant PglB suitable for use in the host cell provided herein include the PglB of SEQ ID NO: 6 comprising the mutation N311V.

The host cell of the invention for use in producing a bioconjugate of an *E. coli* O18 antigen polysaccharide conjugated to a carrier protein further preferably comprises a nucleotide sequence encoding a carrier protein comprising at least one glycosylation site comprising a glycosylation consensus sequence Asn-X-Ser(Thr), more preferably at least one glycosylation site having SEQ ID NO: 4.

In some embodiments, the carrier protein is selected from the group consisting of detoxified Exotoxin A of *P. aeruginosa* (EPA), *E. coli* flagellin (FIIC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

In certain embodiments, the carrier protein is detoxified exotoxin A of *Pseudomonas aeruginosa* (EPA), or CRM197, preferably the carrier protein is EPA. For EPA, various detoxified protein variants have been described in literature and could be used as carrier proteins. In certain embodiments, the EPA carrier proteins used in the conjugates of the invention are modified in such a way that the protein is less toxic and/or more susceptible to glycosylation. For example, detoxification can be achieved by mutating and deleting the catalytically essential residues L552V and ΔE553 according to Lukac et al., 1988, Infect Immun, 56: 3095-3098, and Ho et al., 2006, Hum Vaccin, 2:89-98. In a specific embodiment, the carrier proteins used in the generation of the conjugates of the invention are modified such that the number of glycosylation sites in the carrier proteins is optimized in a manner that allows for lower concentrations of the protein to be administered, e.g., in an immunogenic composition, in its bioconjugate form. In a particular embodiment, the host cell encodes EPA comprising 1-10, preferably 2-4, preferably 4 glycosylation sites comprising a glycosylation consensus sequence having SEQ ID NO: 4. In one embodiment, the carrier protein comprises an amino acid sequence with at least 80, 85, 90, 95, 96, 97, 98 or 99% sequence identity to SEQ ID NO: 3, and comprises 1-10, preferably 2-4, preferably 4 glycosylation sites comprising a glycosylation consensus sequence Asn-X-Ser(Thr), more preferably having SEQ ID NO: 4. In a preferred embodiment, the carrier protein comprises EPA that comprises the amino acid sequence of SEQ ID NO: 3.

In certain preferred embodiments, the host cell according to the invention comprises a nucleotide sequence encoding the oligosaccharyl transferase comprising SEQ ID NO: 6 and a nucleotide sequence encoding the carrier protein comprising SEQ ID NO: 3.

The host cell of the invention for use in producing a bioconjugate of an *E. coli* O18 antigen polysaccharide conjugated to a carrier protein further preferably comprises an *E. coli* O18 rfb locus for synthesis of an O18-antigen polysaccharide structure.

In *E. coli*, the gene products involved in O-antigen biogenesis are encoded by the rfb locus. The host cell as herein provided thus further preferably comprises a nucleotide sequence of an *E. coli* O18 rfb locus, preferably an rfb locus of an *E. coli* strain having serotype O18A. As used herein, "O18 rfb locus" and "O18 rfb gene cluster" refer to a locus in the gram-negative bacterial genome that comprises a cluster of genes that together encode the enzymatic machinery capable of synthesizing an O18-antigen polysaccharide structure. The term rfb locus preferably refers to a genomic locus from the genus *Escherichia*, particularly *E. coli*.

In certain embodiments, the O18 rfb locus is heterologous to the host cell, e.g. introduced into a precursor cell of the host cell, and preferably integrated into the genome thereof. Preferably an original rfb gene cluster, if such was present in a precursor cell, has been replaced by the O18 rfb gene cluster in the host cell, to enable production of bioconjugate of O18.

In certain embodiments, the rfb gene cluster for the *E. coli* O18 antigen polysaccharide is an rfb gene cluster for the *E. coli* O18A antigen polysaccharide. Thus, preferably, an rfb gene cluster for the *E. coli* O18A antigen polysaccharide comprises a nucleotide sequence that is at least 80, 85, 90, 95, 96, 97, 98 or 99% identical to SEQ ID NO: 5, which nucleotide sequence encodes the enzymes that create the *E. coli* O18A antigen polysaccharide and wherein preferably the nucleotide sequence encoding the Wzy O-antigen polymerase is a nucleotide sequence encoding the polypeptide having Wzy O-antigen polymerase activity of the invention, as herein defined above. In certain embodiments the rfb gene cluster comprises the nucleotide sequence of SEQ ID NO: 5 with the exception of the sequence encoding the Wzy O-antigen polymerase, which is a nucleotide sequence encoding the polypeptide having Wzy O-antigen polymerase activity of the invention, as herein defined above. The structure of the repeat unit for *E. coli* O18A antigen polysaccharide is shown as entry (O18A) in Table 1.

Thus, in certain preferred embodiments, a host cell of the invention comprises an *E. coli* rfb gene cluster wherein the nucleotide sequence encoding a Wzy O-antigen polymerase is a nucleotide sequence that encodes a polypeptide having Wzy O-antigen polymerase activity of the invention, as herein defined above. Therefore, in certain preferred embodiments, the endogenous Wzy O-antigen polymerase coding sequence has been replaced by a nucleotide sequence encoding a polypeptide having Wzy O-antigen polymerase activity of the invention the Wzy polymerase of the invention, as herein defined above. Removal of the endogenous Wzy coding sequences and replacement with a sequence coding for a Wzy polymerase of the invention can be achieved by using gene editing techniques as are commonly known in the art.

In one embodiment, the waaL gene is deleted from or functionally inactivated in the genome of a host cell of the invention. The terms "waaL" and "waaL gene" refer to the O-antigen ligase gene encoding a membrane bound enzyme with an active site located in the periplasm. The waaL gene encoded enzyme transfers undecaprenylphosphate (UPP)-bound O antigen to the lipid A core, forming lipopolysaccharide. Deletion or disruption of the endogenous waaL gene (e.g., ΔwaaL strains) disrupts transfer of the O-antigen to lipid A, and can instead enhance transfer of the O-antigen to another available biomolecule, such as a carrier protein expressed in a host cell of the invention.

In one embodiment of a host cell of the invention, the *E. coli* gtrABS genes, which are responsible for O16 O-antigen glucosylation, are deleted from or functionally inactivated in the host cell's genome. In a preferred embodiment, the *E. coli* gtrABS genes are deleted from or functionally inactivated in the genome of an *E. coli* W3110 host cell. While the gtrA and gtrB genes in different serotypes are highly homologous and interchangeable, the gtrS gene encodes a serotype-specific O-antigen glycosyl transferase. In *E. coli* W3110 GtrS can transfer a glucose (Glc) residue to the GlcNAc sugar in the a-L-Rha-(1→3)-D-G1 cNAc motif of the *E. coli* O16 O-antigen.

As will be understood by the skilled person, the polypeptide of the invention comprised in a host cell of the invention, such as the carrier protein, oligosaccharyltransferase, the polypeptide having Wzy O-antigen polymerase activity and the other enzymes of the rfb gene cluster, are conveniently provided to the host cell in the form of nucleic acids encoding the polypeptides of the invention. The nucleic acids encoding the polypeptides of the invention preferably are nucleic acid constructs, specifically expression constructs comprising one or more expression cassettes for expression of the polypeptides of the invention, wherein nucleotide sequences encoding the polypeptides of the invention are operably linked to expression control sequences for expression of the polypeptides in the host cell of the invention. Suitable expression control sequences are referred to above and usually at least include a promoter. The promoter may be a constitutive promoter, or it may be a promoter of which the activity can be regulated, e.g.

repressed or induced upon certain conditions, e.g. temperature changes or presence of certain chemicals or proteins in the cell, all of which are as such well known in the art. The nucleic acid constructs can be extrachromosomal, e.g. a plasmid or other vector, or nucleic acid constructs can be integrated into the genome of the host cell of the invention. Molecular biological methods for the construction and/or synthesis of the nucleic acid constructs for expression of the polypeptides in a host cell of the invention are generally well known in the art. Optionally, the chain lengths of the O-antigens can be manipulated by manipulating the native Wzz O-antigen chain length regulator mechanism, e.g. by over-expression or supplementing a Wzz O-antigen chain regulator, e.g. by replacing an *E. coli* wzzB gene with one of its counterparts from species within *Salmonella* and *Shigella*, or from *P. aeruginosa*, e.g. a *Salmonella enterica* counterpart, fepE or other wzz homolog (see e.g., US 2018/0099038, WO 2020/039359), whereby for instance the number of repeat units of the O-antigen can be increased, with or without additional overexpression of the Wzy protein. The effects of wzz-like genes have been described in literature for these species. None of this is however needed to obtain bioconjugates with good immunogenicity, and in preferred embodiments bioconjugates according to the invention are prepared without manipulation of the Wzz chain length regulator mechanism.

In one embodiment, the yield of an *E. coli* O18 antigen bioconjugate produced with a host cell of the invention comprising a polypeptide having Wzy O-antigen polymerase activity and specific amino acids at indicated positions as defined herein above, is at least 105%, 110%, 120%, 150% or 200% of the yield produced when using the same conditions with an otherwise identical host cell that expresses the reference Wzy O-antigen polymerase having the amino acid sequence of SEQ ID NO: 1.

In one embodiment, the occupancy of glycosylation sites of a *E. coli* O18 antigen bioconjugate produced with a host cell of the invention comprising a polypeptide having Wzy O-antigen polymerase activity and specific amino acids at indicated positions as defined herein above, is improved over the occupancy of glycosylation sites of a bioconjugate produced when using the same conditions with an otherwise identical host cell that expresses the reference Wzy O-antigen polymerase having the amino acid sequence of SEQ ID NO: 1. Thus, in one embodiment, in a composition comprising an *E. coli* O18 antigen bioconjugate produced with a host cell of the invention and of which the carrier protein comprises 4 glycosylation sites, at least 50, 55, 60, 65, or 70% of the bioconjugate molecules are di-, tri- or tetra-glycosylated, i.e. have two to four of the glycosylation sites occupied. Preferably, in this embodiment, the carrier protein comprises an amino acid sequence with at least 80, 85, 90, 95, 96, 97, 98 or 99% sequence identity to SEQ ID NO: 3, comprising 4 glycosylation sites, comprising a glycosylation consensus sequence Asn-X-Ser(Thr), more preferably having SEQ ID NO: 4. Most preferably in this embodiment, the carrier protein comprises an EPA that comprises the amino acid sequence of SEQ ID NO: 3. In certain embodiments such compositions are periplasmic fraction of a host cell producing the O18 bioconjugate. Preferably such compositions comprise not more than 20%, 15%, 10%, of bioconjugates with an average number of about 1-3 repeat units of O18 antigen ('sEPA').

In a further aspect, the invention further relates to methods wherein a host cell of the invention is used for producing a bioconjugate of an *E. coli* O18 antigen polysaccharide conjugated to a carrier protein. Thus, one embodiment pertains to a method for producing a bioconjugate of an *E. coli* O18 antigen polysaccharide conjugated to a carrier protein, wherein preferably, the method at least comprises the step of: a) culturing a host cell of the invention to produce the bioconjugate. In one embodiment, in step a) a host cell of the invention is cultured under conditions conducive to the production of the bioconjugate. In certain embodiments, the method relates to the production of an O18A bioconjugate. The host cell of the invention is cultured under conditions suitable for the expression of a bioconjugate that comprises a carrier protein covalently coupled to *E. coli* O18 antigen polysaccharide, such conditions are known to the person skilled in the art, using methods as for instance previously described in WO 2015/124769 or WO 2020/191082.

In one embodiment, the method for producing the O18 bioconjugate further comprises the step of: b) recovery of the bioconjugate. The O18 bioconjugate can be isolated, separated, and/or purified from recombinant host cells or culture medium using any method known in the art in view of the present disclosure. For example, the O18 bioconjugate can be purified by any method known in the art for purification of a protein, for instance, by chromatography (e.g., ion exchange, anionic exchange, affinity, and sizing column chromatography), centrifugation, differential solubility, or by any other standard technique for the purification of proteins. See, e.g., Saraswat et al., 2013, Biomed. Res. Int., (p. 1-18); see also the methods described in WO 2009/104074. Further, the bioconjugates can be fused to heterologous polypeptide sequences to facilitate purification. Methods to purify and characterize bioconjugates have been described in, e.g., Ihssen et al., 2010, supra, and in WO 2006/119987, WO 2009/104074, and in particular in WO 2015/124769 and WO 2017/035181, and WO2020/191082A1, the disclosures of each of these are incorporated by reference herein.

In one embodiment, the method for producing the O18 bioconjugate further comprises the step of c): formulating the recovered bioconjugate into a pharmaceutical composition. Formulation of the bioconjugate into a pharmaceutical composition will usually involve preparing a composition comprising the bioconjugate of the invention and at least one pharmaceutically acceptable excipient as herein described below in more detail. In one embodiment, the method for producing the O18 bioconjugate further comprises the addition of an adjuvant to the pharmaceutical composition comprising the bioconjugate. Suitable adjuvants for incorporation in a pharmaceutical composition are described herein below in more detail.

In one embodiment, the method for producing the O18 bioconjugate further comprises adding one or more additional conjugates or bioconjugates of *E. coli* O-antigen polysaccharides conjugated to a carrier protein to the pharmaceutical composition to obtain a multivalent composition, preferably a multivalent bioconjugate composition. The one or more additional conjugates of *E. coli* O-antigen polysaccharides conjugated to a carrier protein are thus preferably bioconjugates of *E. coli* O-antigen polysaccharides of serotypes other than O18, or more preferably other than O18A. In a preferred embodiment, the one or more additional conjugates or bioconjugates comprise at least one, two, three, four, five, six, seven, eight or all nine O-antigen polysaccharide selected from the group consisting of *E. coli* serotypes O1, O2, O4, O6, O8, O15, O16, O25 and O75. A detailed description of the *E. coli* O-antigen polysaccharide serotypes is provided herein below (see also Table 1). Such additional conjugates or bioconjugates can be obtained as described before, e.g. as in WO2020/191082A1.

Thus, in one preferred embodiment, the method for producing the O18 bioconjugate further comprises adding additional bioconjugates of *E. coli* O-antigen polysaccharides conjugated to a carrier protein to the pharmaceutical composition to obtain a multivalent composition, wherein the multivalent bioconjugate composition comprises: (i) the bioconjugate of an *E. coli* O18A antigen polysaccharide conjugated to a carrier protein; (ii) a bioconjugate of an *E. coli* O1A antigen polysaccharide conjugated to a carrier protein; (iii) a bioconjugate of an *E. coli* O2 antigen polysaccharide conjugated to a carrier protein; (iv) a bioconjugate of an *E. coli* glucosylated O4 antigen polysaccharide conjugated to a carrier protein; (v) a bioconjugate of an *E. coli* O6A antigen polysaccharide conjugated to a carrier protein; (vi) a bioconjugate of an *E. coli* O15 antigen polysaccharide conjugated to a carrier protein; (vii) a bioconjugate of an *E. coli* O16 antigen polysaccharide conjugated to a carrier protein; (viii) a bioconjugate of an *E. coli* O25B antigen polysaccharide conjugated to a carrier protein; and (ix) a bioconjugate of an *E. coli* O75 antigen polysaccharide conjugated to a carrier protein. In one embodiment, the multivalent bioconjugate composition further comprises: (x) a bioconjugate of an *E. coli* O8 antigen polysaccharide conjugated to a carrier protein. Preferably, in these embodiments, the carrier protein in each bioconjugates (i) to (ix) comprises the amino acid sequence of SEQ ID NO: 3.

In another aspect, the invention pertains to use a host cell of the invention comprising a polypeptide having Wzy O-antigen polymerase activity and specific amino acids at indicated positions as defined herein above (i.e., having (i) I199, K377, and A395; or (ii) T199, K377, and V395; or (iii) T199, K377, and A395; or (iv) I199, K377, and V395; or (v) I199, M377, and A395; wherein in each case the positions are corresponding to positions of SEQ ID NO:1), for improving the occupancy of glycosylation sites of an *E. coli* O18 antigen bioconjugate. The improvement in the occupancy of glycosylation sites of an *E. coli* O18 antigen bioconjugate can for instance be observed by a decrease in the amount of bioconjugates with short repeat units (wherein n in the O18 structure of Table 1 is only about 1-3) and/or preferably by an increase in the amount of bioconjugates that consist of carrier proteins that comprise O18 antigen polysaccharides conjugated to at least two or more N-glycosylation consensus sequences in the carrier protein (and preferably wherein n in the O18 structure of Table 1 is at least 5), as compared to the occupancy of glycosylation sites of a bioconjugate produced when using the same conditions with an otherwise identical host cell that expresses the reference Wzy O-antigen polymerase having the amino acid sequence of SEQ ID NO: 1.

In another aspect, the invention pertains to a bioconjugate of an *E. coli* O18 antigen polysaccharide conjugated to a carrier protein that is obtained or obtainable in a method of the invention for producing the bioconjugate using a host cell of the invention as herein described above.

As used herein, the terms "conjugate", "glycoconjugate" and "bioconjugate" refer to a conjugation product containing an *E. coli* O-antigen covalently bound to a carrier protein. The conjugate of the invention preferably is a bioconjugate, which is a conjugation product produced in a host cell, wherein the O-antigen and the carrier protein are produced biosynthetically by the host cell's machinery, and wherein the O-antigen is also covalently attached to the carrier protein enzymatically, e.g., via N-linkages by the host cell's enzymes.

In yet another aspect, the invention pertains to a composition comprising a bioconjugate of an *E. coli* O18 antigen polysaccharide conjugated to a carrier protein that is obtained or obtainable in a method of the invention for producing the bioconjugate using a host cell of the invention as herein described above.

In one embodiment, a composition comprising a bioconjugate of an *E. coli* O18 antigen conjugated to a carrier protein, is a composition comprising a bioconjugate wherein the carrier protein comprises 4 glycosylation sites, and wherein at least 50, 55, 60, 65, or 70% of the carrier protein molecules in the composition is glycosylated with *E. coli* O18 antigen repeats at at least two of the N-glycosylation sequences, i.e. are di-, tri- or tetra-glycosylated and thus have two to four of the glycosylation sites occupied. Preferably, in this embodiment, the carrier protein comprises an amino acid sequence with at least 80, 85, 90, 95, 96, 97, 98 or 99% sequence identity to SEQ ID NO: 3, comprising 4 glycosylation sites, comprising a glycosylation consensus sequence Asn-X-Ser(Thr), more preferably having SEQ ID NO: 4. Most preferably in this embodiment, the carrier protein comprises an EPA that comprises the amino acid sequence of SEQ ID NO: 3. In certain embodiments such compositions are periplasmic fraction of a host cell producing the O18 bioconjugate. Preferably such compositions comprise not more than 20%, 15%, 10%, of bioconjugates with an average number of about 1-3 repeat units of *E. coli* O18 antigen polysaccharide ('sEPA').

In one embodiment, a composition comprising a bioconjugate of an *E. coli* O18 antigen conjugated to a carrier protein, is a pharmaceutical composition comprising, in addition to the bioconjugate, a pharmaceutically acceptable excipient. The (pharmaceutical) compositions of the invention may comprise any pharmaceutically acceptable excipient including a carrier, filler, preservative, solubilizer and/or diluent. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Further examples of suitable pharmaceutical carriers are well known to the skilled person and have been described in textbooks.

As used herein, the term "pharmaceutically acceptable carrier" refers to a non-toxic material that does not interfere with the effectiveness of a composition according to the invention or the biological activity of a composition according to the invention. A "pharmaceutically acceptable carrier" can include any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the pharmaceutically acceptable carrier will depend on the route of administration for a particular application. According to particular embodiments, in view of the present disclosure, any pharmaceutically acceptable carrier suitable for use in a vaccine can be used in the invention. Suitable excipients include but are not limited to sterile water, saline, dextrose, glycerol, ethanol, or the like and combinations thereof, as well as stabilizers, e.g. Human Serum Albumin (HSA) or other suitable proteins and reducing sugars.

Suitable buffers include Tris-buffered saline, phosphate buffer, and sucrose phosphate glutamate buffer. For example, a Tris-buffered saline (TBS) pH 7.4 (e.g. containing Tris, NaCl and KCl, e.g. at 25 mM, 137 mM and 2.7 mM, respectively); a phosphate buffer comprising about 10 mM $KH_2PO_4/Na_2HPO_4$ buffer at pH of about 7.0, about 5% (w/v) sorbitol, about 10 mM methionine, and about 0.02% (w/v) polysorbate 80; or a phosphate buffer comprising about 10 mM $KH_2PO_4/Na_2HPO_4$ buffer at pH of about 7.0, about 8% (w/v) sucrose, about 1 mM EDTA, and about 0.02% (w/v) polysorbate 80.

Suitable salts include one or more of e.g., Tris-hydrochloride, sodium chloride, calcium chloride, potassium chloride, sodium phosphate, monosodium glutamate, and aluminum salts (e.g., aluminum hydroxide, aluminum phosphate, potassium aluminum sulfate, or a mixture of such aluminum salts).

Suitable preservatives include phenol, benzethonium chloride, 2-phenoxyethanol, or thimerosal at 0.001% to 0.01% (w/v) of the preservative. In other embodiments, no preservative is included.

The compositions may be formulated to be suitable for the intended route of administration to a subject. For example, the compositions can be formulated to be suitable for subcutaneous, parenteral, oral, intradermal, transdermal, colorectal, intraperitoneal, intravaginal, rectal, intravenous, buccal, intranasal, intratracheal, intramuscular, topical, transdermal, or pulmonary administration, preferably intramuscular administration.

The compositions of the invention can be included in a container, pack, or dispenser together with instructions for administration.

In certain embodiments, the compositions of the invention can be stored before use, e.g., the compositions can be stored frozen (e.g., at about −20° C. or at about −70° C.); stored in refrigerated conditions (e.g., at about 2-8° C., e.g. about 4° C.); or stored at room temperature.

The pharmaceutical compositions optionally may comprise, or optionally may be administered in combination with, an adjuvant. The adjuvant for administration in combination with a composition of the invention can be administered before, concomitantly with, or after administration of the immunogenic compositions. In other preferred embodiments, the pharmaceutical compositions of the invention do not comprise an adjuvant, and/or are not administered in combination with an adjuvant.

As used herein, the term "adjuvant" refers to a compound that when administered in conjunction with or as part of a composition of the invention augments, enhances and/or boosts the immune response to a conjugate comprising *E. coli* O18-antigen coupled to a carrier protein, but when the adjuvant compound is administered alone does not generate an immune response to the conjugate. Adjuvants can enhance an immune response by several mechanisms including, e.g., lymphocyte recruitment, stimulation of B and/or T cells, and/or stimulation of antigen presenting cells.

Specific examples of adjuvants include, but are not limited to, aluminum salts (alum) (such as aluminum hydroxide, aluminum phosphate, aluminum sulfate, and aluminum oxide, including nanoparticles comprising alum or nano-alum formulations), calcium phosphate, monophosphoryl lipid A (MPL) or 3-de-O-acylated monophosphoryl lipid A (3D-MPL) (see e.g., United Kingdom Patent GB2220211, EP0971739, EP1194166, U.S. Pat. No. 6,491,919), AS01, AS02, AS03 and AS04 (all GlaxoSmithKline; see e.g. EP1126876, U.S. Pat. No. 7,357,936 for AS04, EP0671948, EP0761231, U.S. Pat. No. 5,750,110 for AS02), imidazopyridine compounds (see WO2007/109812), imidazoquinoxaline compounds (see WO2007/109813), delta-inulin, STING-activating synthetic cyclic-di-nucleotides (e.g. US20150056224), combinations of lecithin and carbomer homopolymers (e.g. U.S. Pat. No. 6,676,958), and saponins, such as Quil A and QS21, optionally in combination with QS7 (e.g. U.S. Pat. No. 5,057,540). In some embodiments, the adjuvant is Freund's adjuvant (complete or incomplete). In certain embodiments, the adjuvant comprises Quil-A, such as for instance commercially obtainable from Brenntag (now Croda) or Invivogen. QuilA contains the water-extractable fraction of saponins from the *Quillaja saponaria* Molina tree. These saponins belong to the group of triterpenoid saponins, that have a common triterpenoid backbone structure. Saponins are known to induce a strong adjuvant response to T-dependent as well as T-independent antigens, as well as strong cytotoxic CD8+ lymphocyte responses and potentiating the response to mucosal antigens. They can also be combined with cholesterol and phospholipids, to form immunostimulatory complexes (ISCOMs), wherein QuilA adjuvant can activate both antibody-mediated and cell-mediated immune responses to a broad range of antigens from different origens. In certain embodiments, the adjuvant is AS01, for example AS01B. AS01 is an adjuvant system containing MPL (3-O-desacyl-4'-monophosphoryl lipid A), QS21 (*Quillaja saponaria* Molina, fraction 21) and liposomes. In certain embodiments, the AS01 is commercially available (GSK) or can be made as described in WO 96/33739, incorporated herein by reference. Certain adjuvants comprise emulsions, which are mixtures of two immiscible fluids, e.g. oil and water, one of which is suspended as small drops inside the other, and are stabilized by surface-active agents. Oil-in-water emulsions have water forming the continuous phase, surrounding small droplets of oil, while water-in-oil oil emulsions have oil forming the continuous phase. Certain emulsions comprise squalene (a metabolizable oil). Certain adjuvants comprise block copolymers, which are copolymers formed when two monomers cluster together and form blocks of repeating units. An example of a water in oil emulsion comprising a block copolymer, squalene and a microparticulate stabilizer is TiterMax®, which can be commercially obtained from Sigma-Aldrich. Optionally emulsions can be combined with or comprise further immunostimulating components, such as a TLR4 agonist. Certain adjuvants are oil in water emulsions (such as squalene or peanut oil) also used in MF59 (see e.g. EP0399843, U.S. Pat. Nos. 6,299,884, 6,451,325) and AS03, optionally in combination with immune stimulants, such as monophosphoryl lipid A and/or QS21 such as in AS02 (see Stoute et al., 1997, N. Engl. J. Med. 336, 86-91). Further examples of adjuvants are liposomes containing immune stimulants such as MPL and QS21 such as in AS01E and AS01B (e.g. US 2011/0206758). Other examples of adjuvants are CpG, and imidazoquinolines (such as imiquimod and R848). See, e.g., Reed G, et al., 2013, Nature Med, 19: 1597-1608. In certain embodiments, the adjuvant is a Th1 adjuvant.

In certain embodiments, the adjuvant comprises saponins, preferably the water-extractable fraction of saponins obtained from *Quillaja saponaria*. In certain embodiments, the adjuvant comprises QS-21.

In certain embodiments, the adjuvant contains a toll-like receptor 4 (TLR4) agonist. TLR4 agonists are well known in the art, see e.g. Ireton G C and S G Reed, 2013, Expert Rev Vaccines 12: 793-807. In certain embodiments, the adjuvant is a TLR4 agonist comprising lipid A, or an analog or derivative thereof.

The adjuvant, for example including a TLR4 agonist, may be formulated in various ways, e.g. in emulsions such as water-in-oil (w/o) emulsions or oil-in-water (o/w) emulsions (examples are MF59, AS03), stable (nano-)emulsions (SE), lipid suspensions, liposomes, (polymeric) nanoparticles, virosomes, alum adsorbed, aqueous formulations (AF), and the like, representing various delivery systems for immunomodulatory molecules in the adjuvant and/or for the immunogens.

The immunostimulatory TLR4 agonist may optionally be combined with other immunomodulatory components, such as saponins (e.g. QuilA, QS7, QS21, Matrix M, Iscoms, Iscomatrix, etc), aluminum salts, activators for other TLRs (e.g. imidazoquinolines, flagellin, dsRNA analogs, TLR9 agonists, such as CpG, etc), and the like (see e.g. Reed et al, 2013, supra).

As used herein, the term "lipid A" refers to the hydrophobic lipid moiety of an LPS molecule that comprises glucosamine and is linked to keto-deoxyoctulosonate in the inner core of the LPS molecule through a ketosidic bond, which anchors the LPS molecule in the outer leaflet of the outer membrane of Gram-negative bacteria. For an overview of the synthesis of LPS and lipid A structures, see, e.g., Raetz, 1993, J. Bacteriology 175:5745-5753, Raetz C R and C Whitfield, 2002, Annu Rev Biochem 71: 635-700; U.S. Pat. Nos. 5,593,969 and 5,191,072. Lipid A, as used herein includes naturally occurring lipid A, mixtures, analogs, derivatives and precursors thereof. The term includes monosaccharides, e.g., the precursor of lipid A referred to as lipid X; disaccharide lipid A; hepta-acyl lipid A; hexa-acyl lipid A; penta-acyl lipid A; tetra-acyl lipid A, e.g., tetra-acyl precursor of lipid A, referred to as lipid IVA; dephosphorylated lipid A; monophosphoryl lipid A; diphosphoryl lipid A, such as lipid A from *Escherichia coli* and *Rhodobacter sphaeroides*. Several immune activating lipid A structures contain 6 acyl chains. Four primary acyl chains attached directly to the glucosamine sugars are 3-hydroxy acyl chains usually between 10 and 16 carbons in length. Two additional acyl chains are often attached to the 3-hydroxy groups of the primary acyl chains. *E. coli* lipid A, as an example, typically has four C14 3-hydroxy acyl chains attached to the sugars and one C12 and one C14 attached to the 3-hydroxy groups of the primary acyl chains at the 2' and 3' position, respectively.

As used herein, the term "lipid A analog or derivative" refers to a molecule that resembles the structure and immunological activity of lipid A, but that does not necessarily naturally occur in nature. Lipid A analogs or derivatives may be modified to e.g. be shortened or condensed, and/or to have their glucosamine residues substituted with another amine sugar residue, e.g. galactosamine residues, to contain a 2-deoxy-2-aminogluconate in place of the glucosamine-1-phosphate at the reducing end, to bear a galacturonic acid moiety instead of a phosphate at position 4'. Lipid A analogs or derivatives may be prepared from lipid A isolated from a bacterium, e.g., by chemical derivation, or chemically synthesized, e.g. by first determining the structure of the preferred lipid A and synthesizing analogs or derivatives thereof. Lipid A analogs or derivatives are also useful as TLR4 agonist adjuvants (see, e.g. Gregg K A et al, 2017, MBio 8, eDD492-17, doi: 10.1128/mBio. 00492-17).

For example, a lipid A analog or derivative can be obtained by deacylation of a wild-type lipid A molecule, e.g., by alkali treatment. Lipid A analogs or derivatives can for instance be prepared from lipid A isolated from bacteria. Such molecules could also be chemically synthesized. Another example of lipid A analogs or derivatives are lipid A molecules isolated from bacterial cells harboring mutations in, or deletions or insertions of enzymes involved in lipid A biosynthesis and/or lipid A modification.

MPL and 3D-MPL are lipid A analogs or derivatives that have been modified to attenuate lipid A toxicity. Lipid A, MPL and 3D-MPL have a sugar backbone onto which long fatty acid chains are attached, wherein the backbone contains two 6-carbon sugars in glycosidic linkage, and a phosphoryl moiety at the 4 position. Typically, five to eight long chain fatty acids (usually 12-14 carbon atoms) are attached to the sugar backbone. Due to derivation of natural sources, MPL or 3D-MPL may be present as a composite or mixture of a number of fatty acid substitution patterns, e.g. hepta-acyl, hexa-acyl, penta-acyl, etc., with varying fatty acid lengths. This is also true for some of the other lipid A analogs or derivatives described herein, however synthetic lipid A variants may also be defined and homogeneous. MPL and its manufacture are for instance described in U.S. Pat. No. 4,436,727. 3D-MPL is for instance described in U.S. Pat. No. 4,912,094B1, and differs from MPL by selective removal of the 3-hydroxymyristic acyl residue that is ester linked to the reducing-end glucosamine at position 3 (compare for instance the structure of MPL in column 1 vs 3D-MPL in column 6 of U.S. Pat. No. 4,912,094B1). In the art often 3D-MPL is used, while sometimes referred to as MPL (e.g. the first structure in Table 1 of Ireton G C and S G Reed, 2013, supra, refers to this structure as MPL®, but actually depicts the structure of 3D-MPL).

Examples of lipid A (analogs, derivatives) include MPL, 3D-MPL, RC529 (e.g. EP1385541), PET-lipid A, GLA (glycopyranosyl lipid adjuvant, a synthetic disaccharide glycolipid; e.g. US20100310602, U.S. Pat. No. 8,722,064), SLA (e.g. Carter D et al, 2016, Clin Transl Immunology 5: e108 (doi: 10.1038/cti.2016.63), which describes a structure-function approach to optimize TLR4 ligands for human vaccines), PHAD (phosphorylated hexaacyl disaccharide; the structure of which is the same as that of GLA), 3D-PHAD, 3D-(6-acyl)-PHAD (3D(6A)-PHAD) (PHAD, 3D-PHAD, and 3D(6A)PHAD are synthetic lipid A variants, see e.g. avantilipids.com/divisions/adjuvants, which also provide structures of these molecules), E6020 (CAS Number 287180-63-6), ONO4007, OM-174, and the like. For exemplary chemical structures of 3D-MPL', RC529, PET-lipid A, GLA/PHAD, E6020, ONO4007, and OM-174, see e.g. Table 1 in Ireton G C and S G Reed, 2013, supra. Fora structure of SLA, see e.g. FIG. 1 in Reed S G et al, 2016, Curr Opin Immunol 41: 85-90. In certain preferred embodiments, the TLR4 agonist adjuvant comprises a lipid A analog or derivative chosen from 3D-MPL, GLA, or SLA. In certain embodiments the lipid A analog or derivative is formulated in liposomes.

Exemplary adjuvants comprising a lipid A analog or derivative include GLA-LSQ (synthetic MPL [GLA], QS21, lipids formulated as liposomes), SLA-LSQ (synthetic MPL [SLA], QS21, lipids, formulated as liposomes), GLA-SE (synthetic MPL [GLA], squalene oil/water emulsion), SLA-SE (synthetic MPL [SLA], squalene oil/water emulsion), SLA-Nanoalum (synthetic MPL [SLA], aluminum salt), GLA-Nanoalum (synthetic MPL [GLA], aluminum salt), SLA-AF (synthetic MPL [SLA], aqueous suspension), GLA-AF (synthetic MPL [GLA], aqueous suspension,), SLA-alum (synthetic MPL [SLA], aluminum salt), GLA-alum (synthetic MPL [GLA], aluminum salt), and several of the GSK ASxx series of adjuvants, including AS01 (MPL, QS21, liposomes), AS02 (MPL, QS21, oil/water emulsion), AS25 (MPL, oil/water emulsion), AS04 (MPL, aluminum salt), and AS15 (MPL, QS21, CpG, liposomes). See, e.g., WO 2013/119856, WO 2006/116423, U.S. Pat. Nos. 4,987,237, 4,436,727, 4,877,611, 4,866,034, 4,912,094, 4,987,237, 5,191,072, 5,593,969, 6,759,241, 9,017,698, 9,149,521, 9,149,522, 9,415,097, 9,415,101, 9,504,743, Reed G, et al., 2013, supra.

Non-glycolipid molecules may also be used as TLR4 agonist adjuvants, e.g. synthetic molecules such as Neoseptin-3 or natural molecules such as LeIF, see e.g. Reed S G et al, 2016, supra.

In one embodiment, a composition of the invention comprising a bioconjugate of an *E. coli* O18 antigen conjugated to a carrier protein, further comprises at least one additional conjugate comprising an *E. coli* O-antigen polysaccharide covalently coupled to a carrier protein. The one or more additional bioconjugates of *E. coli* O-antigen polysaccharides conjugated to a carrier protein preferably are bioconjugates of *E. coli* O-antigen polysaccharides of serotypes other than O18, or more preferably other than O18A. In a preferred embodiment, the one or more additional conjugates or bioconjugates comprise at least one, two, three, four, five, six, seven, eight or all nine O-antigen polysaccharide selected from the group consisting of *E. coli* serotypes O1, O2, O4, O6, O8, O15, O16, O25 and O75.

In a preferred embodiment, the one or more additional *E. coli* O-antigens in the additional conjugate(s) are selected from the group consisting of *E. coli* O1 antigen polysaccharide (e.g. O1A antigen polysaccharide), *E. coli* O2 antigen polysaccharide, *E. coli* O4 antigen polysaccharide (e.g. *E. coli* glucosylated O4 antigen polysaccharide), *E. coli* O6 antigen polysaccharide (e.g. O6A antigen polysaccharide), *E. coli* O8 antigen polysaccharide, *E. coli* O15 antigen polysaccharide, *E. coli* O16 antigen polysaccharide, *E. coli* O25 antigen polysaccharide (e.g. O25A or O25B antigen polysaccharide, preferably O25B antigen polysaccharide), and *E. coli* O75 antigen polysaccharide. Preferably, each of the additional O-antigen polysaccharides is covalently linked to a carrier protein. In certain embodiments, each of the carrier proteins, i.e. the carrier protein for each conjugate, is an EPA carrier protein. Preferably, one or more, preferably all of the additional conjugates are bioconjugates.

As used herein, the term "O18" refers to the O18 antigen of *E. coli* (*E. coli* serotype O18), and could be either O18A, O18B, O18A1, or O18B1 antigen (each of the four subserotypes of *E. coli* serotype O18), and in preferred embodiments O18 refers to O18A. The O18A antigen polysaccharide may comprise the structure of formula (O18A) as shown in Table 1, wherein n is an integer of 1-100, e.g. 3-50, preferably 5-40, e.g. 7 to 25, e.g. 10 to 20. The term "O1A" refers to the O1A antigen of *E. coli* (a subserotype of *E. coli* serotype O1). The term "O2" refers to the O2 antigen of *E. coli* (*E. coli* serotype O2). The term "O4" refers to the O4 antigen of *E. coli* (*E. coli* serotype O4), which may or may not include a glucose side-branch (referred to as Glucosylated O4 antigen polysaccharide (O4-Glc+), and Non-glucosylated O4 antigen polysaccharide (O4-Glc−), respectively; in preferred embodiments O4 is O4-Glc+). The term "O6A" refers to the O6A antigen of *E. coli* (a subserotype of *E. coli* serotype O6). The term "O8" refers to the O8 antigen of *E. coli* (*E. coli* serotype O8). The term "O15" refers to the O15 antigen of *E. coli* (*E. coli* serotype O15). The term "O16" refers to the O16 antigen of *E. coli* (*E. coli* serotype O16). The term "O25B" refers to the O25B antigen from *E. coli* (a subserotype of *E. coli* serotype O25). The term "O75" refers to the O75 antigen of *E. coli* (*E. coli* serotype O75).

The structures of *E. coli* O-antigen polysaccharides referred to throughout this application are shown below in Table 1. A single repeating unit for each *E. coli* O-antigen polysaccharide is shown.

TABLE 1

Structures of *E. coli* O-antigen Polysaccharides

| *E. coli* O-antigen Polysaccharide | Structure of Repeating Unit[1] |
|---|---|
| Non-glucosylated O4 antigen polysaccharide (O4-Glc−) | [→2)-α-L-Rhap-(1→6)-α-D-Glcp-(1→3)-α-L-FucpNAc-(1→3)-β-D-GlcpNAc-(1→]$_n$ |
| Glucosylated O4 antigen polysaccharide (O4-Glc+) | α-D-Glcp<br>1<br>↓<br>3<br>[→2)-α-L-Rhap-(1→6)-α-D-Glcp-(1→3)-α-L-FucpNAc-(1→3)-β-D-GlcpNAc-(1→]$_n$ |
| O1A antigen polysaccharide (O1A) | [→3)-α-L-Rhap-(1→3)-α-L-Rhap-(1→3)-β-L-Rhap-(1→4)-β-D-GlcpNAc-(1→]$_n$<br>2<br>↑<br>1<br>β-D-ManpNAc |
| O2 antigen polysaccharide (O2) | [→3)-α-L-Rhap-(1→2)-α-L-Rhap-(1→3)-β-L-Rhap-(1→4)-β-D-GlcpNAc-(1→]$_n$<br>2<br>↑<br>1<br>α-D-Fucp3NAc |
| O6A antigen polysaccharide (O6A) | [→4)-α-D-GalpNAc-(1→3)-β-D-Manp-(1→4)-β-D-Manp-(1→3)-α-D-GlcpNAc-(1→]$_n$<br>2<br>↑<br>1<br>β-D-Glcp |

TABLE 1-continued

Structures of *E. coli* O-antigen Polysaccharides

| *E. coli* O-antigen Polysaccharide | Structure of Repeating Unit[1] |
|---|---|
| O8 antigen polysaccharide (O8) | α-D-Manp3Me-(1→[3])-β-D-Manp-(1→2)-α-D-Manp-(1→2)-α-D-Manp-(1→]$_n$ |
| O15 antigen polysaccharide (O15) | [→2)-β-D-Galp-(1→3)-α-L-FucpNAc-(1→3)-β-D-GlcpNAc-(1→]$_n$ |
| O16 antigen polysaccharide (O16) | [→2)-β-D-Galf-(1→6)-α-D-Glcp-(1→3)-α-L-Rhap-(1→3)-α-D-GlcpNAc-(1→]$_n$<br>            2<br>            ↑<br>           Ac |
| O18A antigen polysaccharide (O18A) | [→2)-α-L-Rhap-(1→6)-α-D-Glcp-(1→4)-α-D-Galp-(1→3)-α-D-GlcpNAc-(1→]$_n$<br>            3<br>            ↑<br>            1<br>      β-D-GlcpNAc |
| O18B antigen polysaccharide (O18B) | [→3)-α-L-Rhap-(1→6)-α-D-Glcp-(1→4)-α-D-Galp-(1→3)-α-D-GlcpNAc-(1→]$_n$<br>            3<br>            ↑<br>            1<br>      β-D-Glcp |
| O18A1 antigen polysaccharide (O18A1) |                         α-D-Glcp<br>                        1<br>                        ↓<br>                        6<br>[→2)-α-L-Rhap-(1→6)-α-D-Glcp-(1→4)-α-D-Galp-(1→3)-α-D-GlcpNAc-(1→]$_n$<br>            3<br>            ↑<br>            1<br>      β-D-GlcpNAc |
| O18B1 antigen polysaccharide (O18B1) |                         α-D-Glcp<br>                        1<br>                        ↓<br>                        4<br>[→3)-α-L-Rhap-(1→6)-α-D-Glcp-(1→4)-α-D-Galp-(1→3)-α-D-GlcpNAc-(1→]$_n$<br>            3<br>            ↑<br>            1<br>      β-D-Glcp |
| O25B antigen polysaccharide (O25B) |     β-D-Glcp<br>      1<br>      ↓<br>      6<br>[→4)-α-D-Glcp-(1→3)-α-L-Rhap-(1→3)-β-D-GlcpNAc-(1→]$_n$<br>    3              2<br>    ↑              ↑<br>    1             Ac<br>α-L-Rhap |
| O75 antigen polysaccharide (O75) |     β-D-Manp<br>      1<br>      ↓<br>      4<br>[→3)-α-D-Galp-(1→4)-α-L-Rhap-(1→3)-β-D-GlcpNAc-(1→]$_n$ |

[1] Each n is independently an integer of 1 to 100, such as 1-50, 1-40, 1-30, 1-20, and 1-10, 3-50, 3-40, e.g. at least 5, such as 5-40, e.g. 7-30, e.g. 7 to 25, e.g. 10 to 20.

All monosaccharides described herein have their common meaning known in the art. Monosaccharides can have the D or L configuration. If D or L is not specified, the sugar is understood to have the D configuration. Monosaccharides are typically referred to by abbreviations commonly known and used in the art. For example, Glc refers to glucose;

D-Glc refers to D-glucose; and L-Glc refers to L-glucose. Other common abbreviations for monosaccharides include: Rha, rhamnose; GlcNAc, N-acetylglucosamine; GalNAc, N-acetylgalactosamine; Fuc, fucose; Man, mannose; Man3Me, 3-O-methyl-mannose; Gal, galactose; FucNAc, N-acetylfucosamine; and Rib, ribose. The suffix "f" refers to furanose and the suffix "p" refers to pyranose.

A composition comprising the bioconjugate of a carrier protein covalently coupled to *E. coli* O18 antigen polysaccharide according to the invention, may further comprise at least one additional conjugate of a carrier protein covalently coupled to an *E. coli* O-antigen polysaccharide, and in certain embodiments the at least one additional conjugate comprises an *E. coli* O-antigen polysaccharide that is selected from the group consisting of *E. coli* O1A antigen polysaccharide, *E. coli* O2 antigen polysaccharide, *E. coli* O4 antigen polysaccharide, *E. coli* O6A antigen polysaccharide, *E. coli* O8 antigen polysaccharide, *E. coli* O15 antigen polysaccharide, *E. coli* O16 antigen polysaccharide, *E. coli* O25B antigen polysaccharide, and *E. coli* O75 antigen polysaccharide. Such compositions can be prepared by adding together the conjugates to obtain a multivalent conjugate composition. Preferably one or more and preferably all of the additional conjugates are also bioconjugates.

In certain embodiments, an O1A antigen polysaccharide (e.g., in isolated form or as part of a glycoconjugate, preferably a bioconjugate) is present in a (pharmaceutical) composition as provided herein (e.g., a composition comprising the *E. coli* O18 bioconjugate obtained by the method as described herein). The O1A antigen polysaccharide may comprise the structure of formula (O1A) as shown in Table 1, wherein n is an integer of 1-100, e.g. 3-50, preferably 5-40, e.g. 7 to 25, e.g. 10 to 20. Preferably, the O1A antigen polysaccharide is part of a conjugate, more preferably of a bioconjugate, and is covalently linked to a carrier protein, e.g., EPA.

In certain embodiments, an O2 antigen polysaccharide (e.g., in isolated form or as part of a glycoconjugate, preferably a bioconjugate) is present in a (pharmaceutical) composition as provided herein (e.g., a composition comprising the *E. coli* O18 bioconjugate obtained by the method as described herein). The O2 antigen polysaccharide may comprise the structure of formula (O2) as shown in Table 1, wherein n is an integer of 1-100, e.g. 3-50, preferably 5-40, e.g. 7 to 25, e.g. 10 to 20. Preferably, the O2 antigen polysaccharide is part of a conjugate, more preferably of a bioconjugate, and is covalently linked to a carrier protein, e.g., EPA.

In certain embodiments, an O4 antigen polysaccharide (e.g., in isolated form or as part of a glycoconjugate, preferably a bioconjugate) is present in a (pharmaceutical) composition as provided herein (e.g., a composition comprising the *E. coli* O18 bioconjugate obtained by the method as described herein). O-antigen structural modification is known to exist within the *E. coli* O4 serotype. In particular, some O4 serotypes express a modified O-antigen having a branched glucose unit. As used herein, "glucosylated O4 antigen", "glucosylated O4 antigen polysaccharide", "glucose-branched O4", "O4-Glc+ antigen polysaccharide", "Glc+ O4", and "O4-Glc+ antigen" refer to an O4 antigen having a glucose branch. Some O4 serotypes have an O4 antigen without such a branched glucose unit, and this is referred to herein as "non-glucosylated O4 antigen", "non-glucosylated O4 antigen polysaccharide, "O4-Glc– antigen", or "O4-Glc–". When referring to "O4 antigen" herein, this may be either O4-Glc+ antigen or O4-Glc– antigen. In preferred embodiments O4 refers to O4-Glc+ antigen. Structures of *E. coli* non-glucosylated O4 antigen and *E. coli* glucosylated O4 antigen are shown in formulas (O4-Glc–) and (O4-Glc+), respectively, in Table 1, wherein n is an integer of 1 to 100, e.g. 3 to 50, preferably 5 to 40, e.g. 7 to 25, e.g. 10 to 20. Methods to specifically produce O4-Glc+ bioconjugates have been described in WO2020/191082A1 which is herein incorporated in its entirety. Preferably, the O4 antigen polysaccharide is part of a conjugate, more preferably of a bioconjugate, and is covalently linked to a carrier protein, e.g., EPA.

In certain embodiments, an O6A antigen polysaccharide (e.g., in isolated form or as part of a glycoconjugate, preferably a bioconjugate) is present in a (pharmaceutical) composition as provided herein (e.g., a composition comprising the *E. coli* O18 bioconjugate obtained by the method as described herein). The O6A antigen polysaccharide may comprise the structure of formula (O6A) as shown in Table 1, wherein n is an integer of 1-100, e.g. 3-50, preferably 5-40, e.g. 7 to 25, e.g. 10 to 20. Preferably, the O6A antigen polysaccharide is part of a conjugate, more preferably of a bioconjugate, and is covalently linked to a carrier protein, e.g., EPA.

In certain embodiments, an O8 antigen polysaccharide (e.g., in isolated form or as part of a glycoconjugate, preferably a bioconjugate) is present in a (pharmaceutical) composition as provided herein (e.g., a composition comprising the *E. coli* O18 bioconjugate obtained by the method as described herein). The O8 antigen polysaccharide may comprise the structure of formula (O8) as shown in Table 1, wherein n is an integer of 1-100, e.g. 3-50, preferably 5-40, e.g. 7 to 25, e.g. 10 to 20. Preferably, the O8 antigen polysaccharide is part of a conjugate, more preferably of a bioconjugate, and is covalently linked to a carrier protein, e.g., EPA.

In certain embodiments, an O15 antigen polysaccharide (e.g., in isolated form or as part of a glycoconjugate, preferably a bioconjugate) is present in a (pharmaceutical) composition as provided herein (e.g., a composition comprising the *E. coli* O18 bioconjugate obtained by the method as described herein). The O15 antigen polysaccharide may comprise the structure of formula (O15) as shown in Table 1, wherein n is an integer of 1-100, e.g. 3-50, preferably 5-40, e.g. 7 to 25, e.g. 10 to 20. Preferably, the O15 antigen polysaccharide is part of a conjugate, more preferably of a bioconjugate, and is covalently linked to a carrier protein, e.g., EPA.

In certain embodiments, an O16 antigen polysaccharide (e.g., in isolated form or as part of a glycoconjugate, preferably a bioconjugate) is present in a (pharmaceutical) composition as provided herein (e.g., a composition comprising the *E. coli* O18 bioconjugate obtained by the method as described herein). The O16 antigen polysaccharide may comprise the structure of formula (O16) as shown in Table 1, wherein n is an integer of 1-100, e.g. 3-50, preferably 5-40, e.g. 7 to 25, e.g. 10 to 20. Preferably, the O16 antigen polysaccharide is part of a conjugate, more preferably of a bioconjugate, and is covalently linked to a carrier protein, e.g., EPA. A conjugate of an *E. coli* O16 antigen polysaccharide covalently linked to a carrier protein may have a certain degree of acetylation at position 2 of the L-Rha sugar. The degree of this O-acetylation of O16 antigen polysaccharide in a conjugate is preferably at least 30%, preferably at least 50%, such as at least 50%, 55%, 60%, 65%, 70%, 75%, 80%, 85%, 90%, 95%, or 100%.

In certain embodiments, an O25B antigen polysaccharide (e.g., in isolated form or as part of a glycoconjugate, preferably a bioconjugate) is present in a (pharmaceutical)

composition as provided herein (e.g., a composition comprising the E. coli O18 bioconjugate obtained by the method as described herein). The O25B antigen polysaccharide may comprise the structure of formula (O25B) as shown in Table 1, wherein n is an integer of 1-100, e.g. 3-50, preferably 5-40, e.g. 7 to 25, e.g. 10 to 20. Preferably, the O25B antigen polysaccharide is part of a conjugate, more preferably of a bioconjugate, and is covalently linked to a carrier protein, e.g., EPA. Similarly to the O16 antigen polysaccharide as described above, a conjugate of an E. coli O25B antigen polysaccharide covalently linked to a carrier protein may have a certain degree of acetylation at position 2 of the L-Rha sugar. The degree of this O-acetylation of an E. coli O25B antigen polysaccharide in a conjugate is preferably at least 30%, preferably at least 50%, such as at least 50%, 55%, 60%, 65%, 70%, 75%, 80%, 85%, 90%, 95%, or 100%.

In certain embodiments, an O75 antigen polysaccharide (e.g., in isolated form or as part of a glycoconjugate, preferably a bioconjugate) is present in a (pharmaceutical) composition as provided herein (e.g., a composition comprising the E. coli O18 bioconjugate obtained by the method as described herein). The O75 antigen polysaccharide may comprise the structure of formula (O75) as shown in Table 1, wherein n is an integer of 1-100, e.g. 3-50, preferably 5-40, e.g. 7 to 25, e.g. 10 to 20. Preferably, the O75 antigen polysaccharide is part of a conjugate, more preferably of a bioconjugate, and is covalently linked to a carrier protein, e.g., EPA.

In certain embodiments, a composition according to the invention comprises the bioconjugate comprising carrier protein covalently coupled to E. coli O18 antigen polysaccharide according to the invention, and further comprises one or more additional conjugates comprising a carrier protein covalently coupled to an E. coli O-antigen polysaccharide, preferably 4 to 25 of such additional conjugates. Preferably the additional conjugates comprise one or more of the E. coli O-antigen polysaccharides as described above, most preferably at least O25B, O1A, O2, and O6. Particularly preferred are compositions that comprise at least 7, preferably at least 8 additional conjugates, and preferably some and most preferably all of these additional conjugates are bioconjugates.

In preferred embodiments, a composition according to the invention comprises at least the E. coli O1A, O2, O4 (preferably glucosylated O4), O6A, O15, O16, O18 (preferably O18A), O25B and O75 antigen polysaccharides, preferably conjugates of the O1A, O2, glucosylated O4, O6A, O15, O16, O18A, O25B and O75 antigen polysaccharides each independently covalently linked to a carrier protein, e.g., EPA (i.e., an at least 9-valent composition). In certain embodiments, such compositions comprise further an E. coli O8 antigen polysaccharide, preferably in the form of a conjugate, preferably a bioconjugate. In certain embodiments, such compositions (with or without O8 antigen polysaccharide) comprise additional E. coli O-antigen polysaccharides from other serotypes, preferably conjugated to carrier protein, preferably bioconjugates, e.g. from 2-10 additional serotypes. In certain embodiments, pharmaceutical compositions are provided that comprise at least nine bioconjugates, wherein each bioconjugate comprises a carrier protein covalently linked to an E. coli O-antigen polysaccharide from different serotype, wherein the serotypes include O18A (and the O18A bioconjugate is a bioconjugate according to the present invention, that was prepared using a method according to the present invention), O1A, O2, O4-Glc+, O6A, O15, O16, O25B, and O75. In certain embodiments the carrier protein is EPA, e.g. EPA having the amino acid sequence of SEQ ID NO: 3.

Compositions according to the invention may optionally comprise or be combined with or administered together with further proteins, carbohydrates and lipo-saccharides to which an immune response is desired.

In another aspect, the invention relates to a pharmaceutical composition of the invention for use as a medicament.

In a further aspect, the invention relates to the use of a pharmaceutical composition as described herein as a medicament for inducing an immune response against E. coli.

As used herein the terms "immunogen" or "immunogenic" or "antigen" are used interchangeably to describe a molecule to which an immunological response can be generated upon administration to a recipient, either alone, in conjunction with an adjuvant, or presented on a display vehicle.

As used herein, an "immunological response" or "immune response" to an antigen or composition refers to the development in a subject of a humoral and/or a cellular immune response to the antigen or an antigen present in the composition.

In certain embodiments, the pharmaceutical composition as described herein is for use in the prevention or treatment of a disease caused by an E. coli infection. In preferred embodiment, the disease caused by an E. coli infection is invasive extra-intestinal pathogenic E. coli (ExPEC) disease (IED).

As used herein, the term "extra-intestinal pathogenic E. coli" or "ExPEC" refers to genetically related pathogenic E. coli strains that commonly invade, colonize, and induce disease in bodily sites outside of the gastrointestinal tract. ExPEC bacteria include uropathogenic (UPEC) E. coli, newborn meningitic (NMEC) E. coli, septicaemia associated (SePEC) E. coli, adherent invasive (AIEC) E. coli, and avian pathogenic (APEC) E. coli. Diseases associated with ExPEC or ExPEC infections include, but are not limited to, urinary tract infection (UTI), surgical-site infection, bacteremia, abdominal or pelvic infection, such as intra-abdominal infections (IAI), pneumonia, nosocomial pneumonia, osteomyelitis, cellulitis, pyelonephritis, wound infection, meningitis, neonatal meningitis, peritonitis, cholangitis, soft-tissue infections, pyomyositis, septic arthritis, and sepsis.

In a further aspect, the invention pertains to a method of preventing or treating a disease caused by an E. coli infection, in particular an invasive extra-intestinal pathogenic E. coli (ExPEC) disease (IED) in a subject in need therefore, the method comprising the administration of an effective amount of the pharmaceutical composition as described herein.

As used herein, the term "effective amount" refers to an amount of an active ingredient or component that elicits the desired biological or medicinal response in a subject. An effective amount can be determined empirically and in a routine manner, in relation to the stated purpose. For example, in vitro assays can optionally be employed to help identify optimal dosage ranges.

As used herein, "subject" or "patient" means any animal, preferably a mammal, most preferably a human, who will be or has been vaccinated by a method or composition according to an embodiment of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., most preferably a human. In certain embodiments, a subject is a human adult. As used herein, the term "human adult" refers to a human that is 18 years or older. In certain embodiments, the subject is one or more of: (i) a human female between about 16 and about 50 years old, e.g. between about 16 and about 35 years old;
(ii) a human adult more than 50 years old, or more than 55 years old, or more than 60 years old, or more than 65 years old;
(iii) a human subject suffering from reoccurring UTIs;
(iv) a human subject having or at risk of acquiring *E. coli* bacteremia or sepsis;
(v) a human subject that has a condition which requires catheter usage;
(vi) a human subject that undergoes a pre-scheduled surgery;
(vii) a human post-menopausal woman; or
(viii) a human subject that has diabetes.

In yet a further aspect, the invention also relates to the use of the pharmaceutical composition as described herein for the manufacture of a vaccine or a medicament for preventing or treating a disease caused by an *E. coli* infection, in particular an invasive extra-intestinal pathogenic *E. coli* (ExPEC) disease (IED).

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Description of the Sequences

TABLE 2

Sequences

| Description | SEQUENCE | SEQ ID NO. |
|---|---|---|
| Wzy O18 polymerase (amino acid sequence) | MIYILTLTLLLVIAIMFSLLGTKSRITSPLPLHFLPWLLTLIVGISNYDQFYEFNER SFYSLLIWFTVIFIFYFIGELVNYKRENINVYYGLSHIKYECKKYWIIVIPISLYTI FEIYMVGMGGADGFFLNLRLANTLEGYTGKKFILMPAVYPLMMAMFAIVCLTKTSKL NKYSIYFWMFLYCIGTMGKFSILTPILTYLIIYDFKHRLKVKKTIKFTLLIIILALT LHFTRMAENDHSTFLSILGLYIYSPIIALGQLNEVNSSHFGEYTFRFIYAITNKIGL IKELPVNTILDYSYVPVPTNVYTALQPFYQDFGYTGIIFGAVLYGLIYVSLYTAGVR GNNTQALLIYALFSVSSATAFFAETLVTNLAGNVMLVLCTILLWRFTVICKPVQ | 1 |
| Wzy O18 polymerase (nucleic acid sequence) | ATGATATATATATTAACTTTAACTCTTCTTCTAGTTATAGCCATAATGTTTTCTCTT CTCGGCACAAAAAGTAGGATCACATCTCCATTACCTTTGCATTTTTTACCATGGTTA CTAACTTTAATTGTCGGGATAAGTAATTACGATCAATTTTACGAGTTTAATGAAAGA AGCTTTTACTCTTTGTTGATTTGGTTTACAGTTATTTTTATATTTTATTTCATAGGG GAACTGGTTAATTATAAACGTGAAAATATAAATGTTTATTATGGTCTTTCACATATT AAATATGAATGTAAAAAATATTGGATCATTGTCATCCCAATTTCATTATATACCATT TTCGAAATATATATGGTTGGTATGGGGGGAGCAGATGGATTCTTTCTCAATTTACGT CTTGCAAATACATTGGAGGGCTATACGGGTAAAAAATTTATCTTAATGCCTGCTGTA TATCCTCTAATGATGGCTATGTTCGCAATTGTTTGTCTAACAAAAACTTCCAAATTA AATAAATACTCCATTTATTTCTGGATGTTTTTGTATTGTATTGGCACAATGGGAAAA TTTTCAATATTAACGCCAATATTGACATATTTAATTATTTATGACTTCAAACATAGA TTAAAAGTAAAAAAAACAATAAAGTTTACATTGTTGATAATTATATTAGCTTTAACT TTGCATTTTACACGTATGGCTGAGAATGACCACTCAACATTTTTATCTATTTTAGGG CTCTATATTTATTCACCAATAATTGCTTTAGGCCAGTTGAATGAAGTAAATAGTAGT CATTTTGGTGAGTATACGTTTAGATTCATATATGCTATAACTAATAAAATTGGCCTT ATTAAAGAATTGCCAGTAAATACTATTCTTGACTATTCATACGTTCCTGTACCAACA AATGTATATACTGCACTTCAACCATTTTACCAGGATTTTGGTTATACTGGCATCATA TTTGGAGCAGTATTATACGGACTAATATATGTGAGTTTATACACGGCCGGTGTTCGT GGAAATAATACACAGGCATTACTGATTTACGCATTGTTTTCAGTTAGCAGTGCAACG GCTTTCTTCGCTGAAACGCTAGTAACGAATTTAGCTGGAAATGTGATGTTAGTATTA TGTACCATCTTACTATGGCGATTTACAGTAATATGCAAACCAGTACAGTAA | 2 |
| Detoxified EPA protein comprising 4 optimized N-glycosylation sequences | GSGGGDQNATGSGGGKLAEEAFDLWNECAKACVLDLKDGVRSSRMSVDPAIADTNGQ GVLHYSMVLEGGNDALKLAIDNALSITSDGLTIRLEGGVEPNKPVRYSYTRQARGSW SLNWLVPIGHEKPSNIKVFIHELNAGNQLSHMSPIYTIEMGDELLAKLARDATFFVR AHESNEMQPTLAISHAGVSVVMAQAQPRREKRWSEWASGKVLCLLDPLDGVYNYLAQ QRCNLDDTWEGKIYRVLAGNPAKHDLDIKDNNNSTPTVISHRLHFPEGGSLAALTAH QACHLPLEAFTRHRQPRGWEQLEQCGYPVQRLVALYLAARLSWNQVDQVIRNALASP GSGGDLGEAIREQPEQARLALTLAAAESERFVRQGTGNDEAGAASADVVSLTCPVAK DQNRTKGECAGPADSGDALLERNYPTGAEFLGDGGDVSFSTRGTQNWTVERLLQAHR QLEERGYVFVGYHGTFLEAAQSIVFGGVRARSQDLDAIWRGFYIAGDPALAYGYAQD QEPDARGRIRNGALLRVYVPRWSLPGFYRTGLTLAAPEAAGEVERLIGHPLPLRLDA ITGPEEEGGRVTILGWPLAERTVVIPSAIPTDPRNVGGDLDPSSIPDKEQAISALPD YASQPGKPPREDLKLGSGGGDQNAT | 3 |
| Optimized N-glycosylation consensus sequence | Asp(Glu)-X-Asn-Z-Ser(Thr), wherein X and Z arei ndependently selected from any natural amino acid except Pro | 4 |
| the rfb gene cluster of O18A | ATGACGAATTTAAAAGCAGTTATTCCTGTAGCGGGTCTTGGGATGCATATGTTGCCT GCCACTAAGGCGATTCCCAAAGAGATGCTACCGATCGTCGACAAGCCAATGATTCAG TACATCGTTGACGAGATTGTGGCTGCAGGGATCAAAGAAATCCTCCTGGTAACTCAC GCGTCCAAGAACGCGGTCGAAAACCACTTCGACACCTCTTATGAATTAGAATCTCTC | 5 |

TABLE 2-continued

Sequences

| Description | SEQUENCE | SEQ ID NO. |
|---|---|---|
| | CTTGAACAGCGCGTGAAGCGTCAACTGCTGGCGGAAGTACAGTCCATTTGCCCGCCG GGCGTGACAATTATGAACGTGCGTCAGGGCGAACCTTTAGGTTTGGGCCACTCCATT TTATGTGCACGACCTGCCATTGGTGACAATCCATTTGTCGTGGTGCTGCCAGACGTT GTGATCGACGACGCCAGCGCCGACCCGCTGCGCTACAACCTTGCTGCCATGATTGCG CGCTTTAACGAAACTGGCCGCAGCCAGGTTCTGGCAAAACGCATGCCGGGCGATCTC TCTGAATACTCCGTCATCCAGACTAAAGAACCGCTTGATCGCGAAGGTAAAGTCAGC CGCATTGTTGAATTTATCGAAAAACCGGATCAGCCGCAGACCCTGGACTCAGACATC ATGGCTGTAGGGCGTTATGTGCTTTCTGCCGATATTTGGCCTGAACTGGAGCGTACT CAACCTGGAGCATGGGGACGTATTCAGTTGACTGATGCCATTGCTGAGTTGGCAAAA AAACAAGCAGTTGACGCAATGCTGATGACTGGGGACAGTTACGACTGCGGAAAGAAA ATGGGTTATATGCAAGCGTTTGTGAAGTATGGGCTGCGTAACCTAAAAGAAGGGGCG AAGTTCCGTAAAGGGATTGAGAAGCTGTTAAGCGAATAATGAAAATCTGACCGGATG TAACGGTTGATAAGAAAATTATAACGGCAGTGAAGATTAGCGGCGAAAGTAATTTGT TGCGAATTTTCCTGCCGTTGTTTTATATAAACAATCAGAATAACAACGAGTTAGCAA CAGGATTATCGTCAAAGTTTTCCAGGATTTTCCTTGTTTCCAGAGCGGATTGGTAAG ACAATTAGCTTCTGAATTTTTCGGGTTTAGCGCGAGTGGGTAACACTCGTCACATCG TAGGCATGCATGCAGTGCTCTGGTAGCTGTAAAGCCAGGGGCGGTAGCGTGCATTAA TACCTCTATTAATCAAACTGAGAGCCGCTTATTTCACAGCATGCTCTGAAGTAATAT GGAATAAATTAAGTGAAAATACTTGTTACTGGTGGCGCAGGATTTATTGGTTCTGCT GTAGTTCGTCACATTATAAATGATACGCAGGATAGTGTTGTTAATGTCGATAAATTA ACGTACGCCGGAAACCTGGAATCACTTGCAGATGTTTCTGATTCTGAACGCTATTTC TTTGAACATGCGGATATTTGTGATGCAGCTGCAATGGCACGGATTTTTGCTCAGCAT CAGCCGGATGCAGTGATGCACCTGGCAGCTGAAAGCCATGTTGACCGTTCAATTACA GGCCCTGCGGCATTTATTGAAACCAATATTGTTGGTACTTATGTCCTTTTAGAAGCG GCTCGGAATTACTGGTCTGCACTTGATGGCGACAAGAAAAACAGCTTCCGTTTTCAT CATATTTCTACTGACGAAGTCTATGGTGATTTGCCTCATCCTGACGAGGTAAATAAT AAAGAAGGATTACCCTTATTTACTGAGACGACAGCCTACGCACCAAGCAGCCCTTAT TCTGCATCAAAAGCGTCCAGCGATCATTTAGTCCGTGCGTGGAAACGTACCTATGGT TTACCGACCATTGTGACTAATTGCTCTAACAATTATGGTCCTTATCATTTCCCGGAA AAATTGATTCCATTGGTTATTCTGAATGCTCTGGAAGGTAAAGGATTACCTATTTAT GGAAAAGGCGATCAAATTCGCGACTGGCTGTATGTTGAAGATCATGCGCGTGCGTTA TATACCGTCGTAACCGAAGGTAAAGCGGGTGAAACTTATAACATTGGTGGACACAAC GAAAAGAAAAACATCGATGTAGTGCTCACTATTTGTGATTTGTTGGATGAGATTGTC CCGAAAGAGAAATCTTACCGCGAGCAAATTACTTATGTTGCCGATCGTCCGGGACAC GATCGACGTTATGCGATTGATGCTGAGAAGATTGGTCGCGAATTGGGATGGAAACCA CAGGAAACGTTTGAGAGCGGGATTCGTAAAACTGTGGAATGGTATCTGTCCAATACA AAATGGGTTGATAATGTGAAAAGTGGTGCCTATCAATCGTGGATTGAACAGAACTAT GAGGGCCGCCACTAATGAATATCCTCCTTTTTGGCAAAACAGGGCAGGTTGGTTGGG AACTACAGCGTGCTCTGGCACCTCTGGGTAATTTGATTGCTCTTGATGTTCACTCCA CTGATTACTGTGGTGATTTTAGTAACCCTGAAGGTGTGGCTGAAACCGTTAGAGCA TTCGGCCTGATATTATTGTCAACGCAGCCGCTCACACCGCAGTAGACAAAGCAGAAT CAGAACCGGAGTTTGCACAATTACTGAACGCGACGAGTGTCGAAGCGATCGCGAAAG CAGCCAATGAAGTCGGCGCTTGGGTTATTCACTACTCTACTGACTACGTATTTCCGG GGACCGGTGAAATACCATGGCAGGAGGAGGATGCAACCGCACCGCTAAATGTTTACG GTGAAACCAAGTTAGCAGGAGAAAAAGCATTACAAGAGCATTGTGCGAAGCACCTTA TTTTCCGGACCAGCTGGGTCTATGCAGGTAAAGGAAATAACTTCGCCAAAACGATGT TGCGTCTGGCAAAAGAGCGTGAAGAATTAGCCGTTATTAATGATCAGTTTGGTGCGC CAACTGGCGCAGAGTTGCTGGCTGATTGTACGGCACATGCCATTCGTGTGGCACTGA ATAAACCGGAAGTCGCAGGTTTGTACCATCTGGTAGCCAGTGGTACCACAACCTGGC ACGATTATGCTGCGCTGGTTTTTGAAGAGGCGCGCAAAGCAGGCATTCCCCTTGCAC TCAACAAGCTCAACGCAGTACCAACAACAGTCTATCCTACACCAGCTCGTCGTCCAC ATAACTCTCGCCTTAATACAGAAAAATTTCAGCAGAACTTTGCGCTTGTCTTGCCTG ACTGGCAGGTTGGTGTGAAACGCATGCTCAACGAATTATTTACGACTACAGCAATTT AATAGTTTTTGCATCTTGTTCGTGATGGTGGAACAAGATGAATTAAAAGGAATGATG GAATGAAAACGCGTAAAGGTATTATTTTAGCGGGTGGTTCTGGTACACGTCTTTATC CTGTGACTATGGCTGTCAGTAAACAGCTGTTACCGATTTATGATAAACCGATGATCT ATTACCCGCTCTCTACACTGATGTTGGCGGGTATTCGCGATATTTTGATTATCAGCA CGCCACAGGATACTCCTCGTTTTCAACAACTGCTGGGTGATGGGAGCCAGTGGGGGC TAAATCTTCACTACAAAGTGCAACCGAGTCCGGATGGTCTTGCGCAGGCATTTATCA TCGGTGAAGAGTTTATCGGTGGTGATGATTGTGCTTTGGTACTTGGTGATAATATCT TCTACGGTCACGACCTGCCTAAGTTAATGGATGCCGCTGTTAACAAAGAAAGTGGTG CAACGGTATTTGCCTATCACGTTAATGATCCTGAACGCTATGGTGTCGTTGAGTTTG ATAAAAACGGTACGCAATTAGCCTGAAGAAAAACCGCTACAACCAAAAGTAATT ATGCAGTAACCGGGCTTTATTTCTATGATAACTACGTTGTGGAAATGGCGAAAAATC TTAAGCCTTCTGCCCGCGGTGAACTGGAAATTACCGATATTAACCGTATTTATATGG AACAGGGGCATTTATCTGTTGCCATGATGGGACGTGGTTATGCATGGCTGGACACGG GGACACATCAGAGTCTTATTGAAGCAAGCAACTTCATTGCCACCATTGAAGAGCGCC AGGGACTAAAGGTTTCCTGCCCAGAAGAAATTGCTTATCGTAAAGGATTATTGACG CAGAGCAGGTTAAGGTATTAGCCGAACCGCTGAAGAAAAACGCTTATGGTCAGTATT TGCTGAAAATGATTAAAGGTTAGTAATAAAATGAATGTTATTAAAACAGAAATTCCA GACGTACTGATTTTTGAACCGAAAGTTTTTGGTGACGAGCGCGTTTCTTTTTCGAA AGCTATAACCAGAGGGTTTTGAGGAAGCTGTAGGTCGCAAAGTTGAGTTTGTTCAG GATAACCATTCTAAATCGAGAAAGGAGTATTGCGGGATTGCATTATCAATTAGAG CCGTATGCGCAAGCAAAACTTGTGCGTTGCATTGAGGGTGAAGTATTTGATATTGCT | |

TABLE 2-continued

Sequences

| Description | SEQUENCE | SEQ ID NO. |
|---|---|---|
| | GTAGATATACGGAAGTCATCTCCATTTTTTGGTAAATGGGTTGGTGTAACATTATCC | |
| | GCTGAAAATAAACGTCAATTATGGATCCCTGAAGGGTTTGCTCATGGTTTTGTGGTG | |
| | ATTAGTGATACTGCGGAATTTGTCTATAAAACGAACAATTATTACAGTCAACAAGCA | |
| | GAGCGAAGCATAATTTTTGATGATAAAGACTTAGGGATTGCTTGGCCATTGAATACT | |
| | CATTATATTCTTTCAGAAAAAGATTTAAATGCGCCAACATTTAAGAAAATATCGAGT | |
| | AATGAGTATTTTAAATGAGTTTAATCAAAAACAGTTTTTGGAACCTTTGCGGGTATG | |
| | TACTTCCAGCTATTGTGACACTACCAGCTTTGGGTATTATGGGGCGAAAATTAGGCC | |
| | CAGAATTATTTGGTGTATTCACTTTGGCATTAGCTGTTGTGGGTTATGCAAGCATTT | |
| | TTGATGCAGGCCTTACTCGCGCAGTGATACGAGAAGTCGCAATTGAAAAAGATAATG | |
| | AAGAAAATAAGTTGAAAATTATTTCTTCAGCGACAGTTGTAATTATTTATTTGAGTT | |
| | TGGCCGCCTCACTCTTATTATTTTTTTTAGTGGTCATATCGCATTGCTACTGAACA | |
| | TTAGTGAGACTTTTTTTCATAATGTAAGTGTCTCGCTTAAAATTCTCGCAGCATCCA | |
| | TACCATTATTTTTGATTACTCAAATATGGTTGTCAATTTTAGAAGGTGAAGAAAGAT | |
| | TTGGTTTACTTAATATCTACAAATCAATTACGGGAGTGATATTAGCAATCTCACCGG | |
| | CATTATTTATACTTATTAAACCCTCTTTGATGTATGCGATAATAGGCTTAGTTCTAG | |
| | CAAGGTTTTTATGTTTTATTTTGGCTTTTATAATTTGTCACGATAAAGTGCTTAAAG | |
| | CTAAACTAACAATCGATATACCAACAATTAAAAGATTGTTTATGTTCGGTGGTGGA | |
| | TTACAGTAAGTAATATCATCAGCCCTGTGCTATCATATTTTGATAGGTTTATTGTTT | |
| | CAAATCAACTTGGGGCTGCTAATGTTGCTTTTTATACTGCACCATCAGAAATTATTT | |
| | CTCGGCTTAGTATAATTCCAGGTGCGTTTTCAAGAGCCTTATTTCCAAGATTAGCTA | |
| | ATGCAAATAATTCCGCTGAAAGATATAAAACGAAAAGATTAATTACAATTTCACTTT | |
| | TAATAATCATCACCCCTATTTTTTGTATTGGCGTGTTATTTTCAGAGAAGATAATGG | |
| | TTTTATGGATGGGGGCATCATTTTTTGGTGAGCCTGGTTTGGTATTATCAATATTAC | |
| | TGATTGGCTTTATTTTTAATGGATTGGCACAAGTACCATTTGCCAGTATTCAATCCC | |
| | GAGGTCATGCTAAGATAACTGCATTTGTTCATCTCTTAGAGTTGTTTCCTTATTTAT | |
| | TACTTTTATTTTACCTCATAAAAGCACATGGGGTTGTTGGCGCGGGTATTGCGTGGT | |
| | CAGTGAGGATGATAGTAGATTATATAGCATTAAGTCTTTTGGACGGTAAGTATATTA | |
| | ATAAATAAATTCAAATGCAAGTTAATAACTCATGGCTTTATTTGGGTAGGTGACA | |
| | ATTTATAATGATATATATATTAACTTTAACTCTTCTTCTAGTTATAGCCATAATGTT | |
| | TTCTCTTCTCGGCACAAAAAGTAGGATCACATCTCCATTACCTTTGCATTTTTACC | |
| | ATGGTTACTAACTTTAATTGTCGGGATAAGTAATTACGATCAATTTTACGAGTTTAA | |
| | TGAAAGAAGCTTTTACTCTTTGTTGATTTGGTTTACAGTTATTTTTATATTTTATTT | |
| | CATAGGGGAACTGGTTAATTATAAACGTGAAAATATAAATGTTTATTATGGTCTTTC | |
| | ACATATTAAATATGAATGTAAAAAATATTGGATCATTGTCATCCCAATTTCATTATA | |
| | TACCATTTTCGAAATATATATGGTTGGTATGGGGGGAGCAGATGGATTCTTTCTCAA | |
| | TTTACGTCTTGCAAATACATTGGAGGGCTATACGGGTAAAAAATTTATCTTAATGCC | |
| | TGCTGTATATCCTCTAATGATGGCTATGTTCGCAATTGTTTGTCTAACAAAAACTTC | |
| | CAAATTAAATAAATACTCCATTTATTTCTGGATGTTTTTGTATTGTATTGGCACAAT | |
| | GGGAAAATTTTCAATATTAACGCCAATATTGACATATTTAATTATTTATGACTTCAA | |
| | ACATAGATTAAAAGTAAAAAAAACAATAAAGTTTACATTGTTGATAATTATATTAGC | |
| | TTTAACTTTGCATTTTACACGTATGGCTGAGAATGACCACTCAACATTTTTATCTAT | |
| | TTTAGGGCTCTATATTTATTCACCAATAATTGCTTTAGGCCAGTTGAATGAAGTAAA | |
| | TAGTAGTCATTTTGGTGAGTATACGTTTAGATTCATATATGCTATAACTAATAAAAT | |
| | TGGCCTTATTAAAGAATTGCCAGTAAATACTATTCTTGACTATTCATACGTTCCTGT | |
| | ACCAACAAATGTATATACTGCACTTCAACCATTTTACCAGGATTTTGGTTATACTGG | |
| | CATCATATTTGGAGCAGTATTATACGGACTAATATATGTGAGTTTATACACGGCCGG | |
| | TGTTCGTGGAAATAATACACAGGCATTACTGATTTACGCATTGTTTTCAGTTAGCAG | |
| | TGCAACGGCTTTCTTCGCTGAAACGCTAGTAACGAATTTAGCTGGAAATGTGATGTT | |
| | AGTATTATGTACCATCTTACTATGGCGATTTACAGTAATATGCAAACCAGTACAGTA | |
| | ACCATTCTAATGGCCACCTACAATGGCGAGGCCTTCATCAAAAATCAGATTTTGTCA | |
| | CTACAACAACAAACATTTTCTAACTGGCGGTTATTTATTCAGGATGATGGGTCTACA | |
| | GACAATACTATATCTATAATAAAAAACTTCCAAAAATCTGACTCCAGAATTCGGCTA | |
| | GTTGATGATAATTTGAAAGGTCAAGGTGCAGGAAAAAATTTTTTATCGCTGATAAAG | |
| | TACAGCGAGACAGATTATACAATTTATTGTGACCAAGATGATATTGGTTAGAAAAC | |
| | AAAAATATTTGAATTAGTAAAGTATGCAAATGAAATTAAATTGAATGTATCAGATGCG | |
| | CCTTCGCTAGTTTATGCTGATGGCTATGCTTATATGGATGGTGAGGGTACAATCGAT | |
| | TTTTCTGGGATATCTAACAATCATGCTGATCAATTAAAGGATTTTCTTTTTTTTAAT | |
| | GGTGGATACCAAGGATGTTCTATTATGTTCAATCGTGCAATGACCAAATTTCTTCTG | |
| | AATTATCGAGGATTTGTATATCTACATGACGATATCACAACATTAGCTGCATACGCT | |
| | CTTGGTAAAGTTTATTTTCTCCCGAAATACCTTATGTTATATAGACAGCACACGAAT | |
| | GCGGTAACTGGTATCAAAACATTCCGCAATGGATTGACTTCTAAATTTAAATCACCA | |
| | GTAAACTATCTTTTATCACGAAAACATTATCAGGTAAAAAATCTTTTTTTGAATGT | |
| | AACAGCTCTATCTTATCAGAGACGAATAAAAAAGTTTTTTGGATTTTATTTCATTT | |
| | TGTGAATCAAATAATAAATTTACAGATTTTTTAAGTTATGGCGAGGTGGGTTTAGA | |
| | TTAAATAACAGTAGAACTAAATTATTATTAAAATTCTTAATACGGAGAAAATTTAGC | |
| | GAATGATTTCAATACTTACACCTACTTTTAATCGGCAACATACTTTATCAAGGCTAT | |
| | TCAATTCTCTTATATTACAAACTGATAAAGATTTTGAGTGGATAATAATTGATGATG | |
| | GTAGTATAGATGCAACAGCGGTACTTGTAGAAGATTTTAGAAAAAAATGTGATTTTG | |
| | ACTTGATTTATTGCTATCAGGAAAATAATGGTAAGCCCATGGCTTTAAACGCTGGTG | |
| | TTAAAGCTTGTAGAGGCGATTATATCTTTATTGTTGACAGTGATGATGCACTAACTC | |
| | CCGATGCCATAAAATTAATTAAAGAATCAATACATGATTGCTTATCTGAGAAGGAAA | |
| | GTTTCAGCGGAGTCGGTTTTAGAAAAGCATATATAAAAGGGGGATTATTGGTAATG | |
| | ATTTAAATAATTCTTCAGAACATATATACTATTTAAATGCGACTGAGATTAGCAATT | |
| | TAATAAATGGTGATGTTGCATATTGTTTTAAAAAAGAAAGTTTGGTAAAAAATCCAT | |

TABLE 2-continued

Sequences

| Description | SEQUENCE | SEQ ID NO. |
|---|---|---|
| | TCCCCCGTATAGAAGATGAAAAATTTGTTCCAGAATTATATATTTGGAATAAAATAA | |
| | CTGACAAGGCGAAGATTCGATTTAACATAAGCAAAGTTATATATCTTTGTGAGTATC | |
| | TTGATGATGGTCTTTCTAAAAATTTCCATAACCAGCTTAAAAAATACCCAAAGGGGT | |
| | TTAAGATTATTACAAAGATCAAAGAAAACGAGAGAAAACTTATATAAAAAAAACAA | |
| | AGATGCTAATTAGATATTTGCAATGTTGTTATTATGAGAAAATAAAATGAAAATACT | |
| | ATTTGTCATTACAGGTTTAGGCCTTGGAGGTGCTGAGAAGCAGGTTTGTCTTTTAGC | |
| | TGATAAATTAAGTTTAAGCGGGCACCATGTAAAGATTATTTCACTTGGACATATGTC | |
| | TAATAATAAAGTCTTTCCTAGCGAAAATAATGTTAATGTCATTAATGTAAATATGTC | |
| | AAAAAAACATTTCTGGAGTTATAAAAGGTTGTGTCAGAATTAGAGATGTTATAGCTAA | |
| | TTTCAAACCAGACATTGTACACAGTCATATGTTTCATGCAAACATTATCACTAGATT | |
| | GTCTGTAATTGGAATCAAAAACAGACCTGGTATTATATCAACTGCACATAATAAAAA | |
| | TGAAGGTGGGTATTTCAGAATGCTCACATATAGAATAACCGATTGTTTAAGTGATTG | |
| | TTGTACAAATGTTAGCAAAGAAGCAGTGGATGAGTTTTTACGGATAAAAGCCTTTAA | |
| | TCCCGCTAAAGCAATTACTATGTATAATGGGATAGATACCAATAAATTTAAATTTGA | |
| | TTTATTGGCAAGGAGGGAAATTCGAGACGGTATTAATATAAAAAATGATGATATATT | |
| | ATTACTTGCTGCAGGTCGTTTAACGTTAGCTAAAGATTATCCTAATTTATTGAATGC | |
| | AATGACTCTGCTTCCTGAACACTTTAAACTTATTATTATTGGTGATGGTGAATTGCG | |
| | TGACGAAATTAATATGCTTATAAAAAAATTGCAATTATCTAATAGGGTGTCCTTGTT | |
| | GGGAGTTAAAAAAAATATTGCTCCCTATTTTCTGCATGTGATATTTTTGTTCTCTC | |
| | TTCTCGTTGGGAAGGATTTGGATTAGTCGTGGCAGAAGCTATGTCATGTGAGCGAAT | |
| | TGTTGTTGGCACGGATTCAGGGGGAGTAAGAGAAGTTATTGGTGACGATGATTTTCT | |
| | TGTACCCATATCTGATTCAACACAACTTGCAAGCAAAATTGAAAAATTGTCTTTGAG | |
| | CCAGATACGTGATCACATTGGTTTTCGGAATCGTGAGCGTATTTTAAAAAATTTCTC | |
| | AATAGATACTATTATTATGCAGTGGCAAGAACTCTATGGAACTATAATTTGCTCAAA | |
| | ACATGAAAGGTAGATTTATATTTGGAACGTGTCTTTTGTTTGAATTTAATTCAATCT | |
| | CAATTGAGATTTTTGTATTTCAAAAATACCATCATAGCTAACGATGATTGGTATTTA | |
| | TTTTAAGATGCTTTCTATAAATATATTGACGTTTTTAATGCGCCGAAACGATTGGGC | |
| | TGGGAACAGAGAAGTAAAACTGTTTTGAGAATGAAGAGTTTTTGAGATGTTTATGGA | |
| | TATTAAAAATTGATCCAGTGAATTAATTATTTATAATAAATCAAGATTTAATGTTAA | |
| | TAAATGATAATCTTTTCTGACACTCATATTAATTATGAGTGGTACGTTTGGTAAACG | |
| | GTAAACTATTATATGACAGCTAGAACAACTAAAGTTTTGCACTTACAATTACTCCCA | |
| | CTCTTAAGTGGCGTTCAAAGGGTAACATTAAACGAAATTAGTGCGTTATATACTGAT | |
| | TATGATTATACACTAGTTTGCTCAAAAAAGGTCCACTAACAAAAGCATTGCTGGAA | |
| | TATGATGTCGATTGTCATTGTATCCCCGAACTTACGAGAGAAATTACCGTAAAGAAT | |
| | GATTTTAAAGCATTGTTCAAGCTTTATAAGTTCATAAAAAAAGAAAAATTTGACATT | |
| | GTGCATACACATTCTTCAAAAACAGGTATTTTGGGGCGAGTTGCTGCCAAATTAGCA | |
| | CGTGTTGGAAAGGTGATCCACACTGTACATGGTTTTTCTTTTCCAGCCGCATCTAGT | |
| | AAAAAAAGTTATTACCTTTATTTTTTCATGGAATGGATAGCAAAGTTCTTTACGGAT | |
| | AAGTTAATCGTCTTGAATGTAGATGATGAATATATAGCAATAAACAAATTAAAATTC | |
| | AAGCGGGATAAAGTTTTTTTAATTCCTAATGGAGTAGACACTGATAAGTTTTCTCCT | |
| | TTAGAAAATAAAATTTATAGTAGCACCTTGAATCTAGTAATGGTTGGTAGATTATCC | |
| | AAGCAAAAAGATCCTGAGACATTATTGCTTGCTGTTGAAAAACTGCTGAATGAAAAT | |
| | GTTAATGTTAAGCTGACACTTGTAGGAGATGGTGAACTAAAAGAACAGTTAGAAAGC | |
| | AGGTTCAAACGGCAAGATGGACGTATAATTTTTCATGGATGGTCAGATAACATTGTT | |
| | AATATTTTAAAAGTTAATGATCTTTTTATATTACCTTCTCTTTGGGAGGGTATGCCA | |
| | TTAGCAATTTTAGAAGCATTGAGCTGTGGACTTCCATGTATAGTCACTAATATTCCA | |
| | GGTAATAATAGCTTAATAGAAGATGGCTATAATGGTTGTTTGTTTGAAATTAGAGAT | |
| | TGTCAGTTATTATCTCAAAAAATCATGTCATATGTTGGTAAGCCAGAACTGATTGCA | |
| | CAGCAATCTACCAATGCACGATCATTTATTCTGAAAAATTATGGATTAGTTAAAGA | |
| | AATAATAAGGTCAGACAGCTATATGATAATTAAATGAAACCGAAAAGTTAAAAAAGA | |
| | ACAGGTTTTTCAAAGTGAAAATAAAATTCAGTTTTTTATTGCAATGATTAACGTA | |
| | ACATCTGCATTACATTCAAGCCGCACAACCCCGCGGTGACCATCCCTGACAGGAGTA | |
| | AACAATGTCAAAGCAACAGATCGGCGTCGTCGGATGGCAGTGATGGGACGCAACCT | |
| | CGCGCTCAACATCGAAAGCCGTGGTTATACCGTCTCTATTTTCAACCGTTCCCGTGA | |
| | AAAGACGGAAGAAGTTATTGCCGAAAATCCAGGCAAGAAACTGGTTCCTTACTATAC | |
| | GGTGAAAGAGTTCGTTGAATCTCTTGAAACGCCTCGTCGCATCCTGTTAATGGTTAA | |
| | AGCAGGTGCAGGCACGGATGCTGCTATTGATTCCCTGAAACCATATCTCGATAAAGG | |
| | CGATATCATCATTGATGGTGGTAATACCTTCTTCCAGGACACCATTCGTCGTAACCG | |
| | CGAGCTTTCTGCACAAGGCTTTAACTTCATCGGTACGGGTGTTTCCGGTGGTGAAGA | |
| | GGGCGCGCTGAAAGGACCTTCTATCATGCCTGGTGGGCAGAAAGAGGCCTATGAACT | |
| | GGTTGCTCCTATCCTGACCAAAATCGCCGCCGTGGCTGAAGATGGTGAACCATGCGT | |
| | TACCTATATTGGTGCCGATGGCGCAGGTCACTATGTGAAGATGGTTCACAACGGTAT | |
| | TGAATACGGTGATATGCAACTGATTGCTGAAGCCTATTCTCTGCTGAAAGGTGGTCT | |

TABLE 2-continued

Sequences

| Description | SEQUENCE | SEQ ID NO. |
|---|---|---|
| | GAATCTCTCTAACGAAGAACTGGCACAAACCTTTACCGAGTGGAATAACGGTGAACT<br>GAGCAGTTACCTGATCGACATCACTAAAGACATCTTCACCAAAAAAGATGAAGACGG<br>TAACTACCTGGTTGATGTGATCCTGGATGAAGCAGCAAACAAAGGTACGGGTAAATG<br>GACCAGTCAGAGCGCGCTGGATCTCGGTGAGCCACTGTCGCTGATTACTGAGTCTGT<br>GTTTGCACGCTACATCTCTTCACTAAAAGATCAGCGCGTGGCTGCGTCTAAAGTACT<br>GTCGGGTCCACAAGCGCAGCCAGCAGGCGACAAAGCAGAGTTCATTGAAAAAGTTCG<br>CCGTGCGCTTTATCTGGGTAAGATTGTTTCTTACGCGCAGGGCTTCTCTCAGCTGCG<br>TGCTGCGTCTGAAGAGTACAACTGGGATCTGAACTACGGTGAAATCGCGAAGATTTT<br>CCGTGCTGGCTGCATCATCCGTGCGCAGTTCCTGCAGAAAATCACCGATGCTTATGC<br>CGAAAATCCGCAGATCGCTAACCTGCTGCTGGCTCCGTACTTCAAGCAAATTGCCGA<br>TGACTACCAGCAGGCTCTGCGTGATGTCGTTGCTTATGCAGTACAGAACGGTATCCC<br>GGTTCCGACCTTCGCCGCTGCGGTTGCCTATTACGATAGCTACCGTGCCGCTGTTCT<br>GCCTGCGAACCTGATCCAGGCACAGCGTGACTATTTCGGTGCACATACTTATAAGCG<br>CATTGATAAAGAAGGTGTGTTCCATACTGAATGGCTGGATTGA | |
| PglB oligo-<br>saccharyl<br>transferase | MLKKEYLKNPYLVLFAMIILAYVFSVFCRFYWVWWASEFNEYFFNNQLMIISNDGYA<br>FAEGARDMIAGFHQPNDLSYYGSSLSALTYWLYKITPFSFESIILYMSTFLSSLVVI<br>PTILLANEYKRPLMGFVAALLASIANSYYNRTMSGYYDTDMLVIVLPMFILFFMVRM<br>ILKKDFFSLIALPLFIGIYLWWYPSSYTLNVALIGLFLIYTLIFHRKEKIFYIAVIL<br>SSLTLSNIAWFYQSAIIVILFALFALEQKRLNFMIIGILGSATLIFLILSGGVDPIL<br>YQLKFYIFRSDESANLTQGFMYFNVNQTIQEVENVDLSEFMRRISGSEIVFLFSLFG<br>FVWLLRKHKSMIMALPILVLGFLALKGGLRFTIYSVPVMALGFGFLLSEFKAIMVKK<br>YSQLTSNVCIVFATILTLAPVFIHIYNYKAPTVFSQNEASLLNQLKNIANREDYVVT<br>WWDYGYPVRYYSDVKTLVDGGKHLGKDNFFPSFALSKDEQAAANMARLSVEYTEKSF<br>YAPQNDILKTDILQAMMKDYNQSNVDLFLASLSKPDFKIDTPKTRDIYLYMPARMSL<br>IFSTVASFSFINLDTGVLDKPFTFSTAYPLDVKNGEIYLSNGVVLSDDFRSFKIGDN<br>VVSVNSIVEINSIKQGEYKITPIDDKAQFYIFYLKDSAIPYAQFILMDKTMFNSAYV<br>QMFFLGNYDKNLFDLVINSRDAKVFKLKI | 6 |

EXAMPLES

The following examples of the invention are to further illustrate the nature of the invention. It should be understood that the following examples do not limit the invention and that the scope of the invention is to be determined by the appended claims.

A bioconjugation system in *E. coli* has been developed recently, in which the antigen polysaccharide and the carrier protein are both synthesized in vivo and subsequently conjugated in vivo through the activities of the oligosaccharyl transferase PglB, a *Campylobacter jejuni* enzyme, expressed in *E. coli* (Wacker et al., Proc. Nat. Acad. Sci. (2006) v. 103, pp. 7088-93). This N-linked protein glycosylation system is capable of the transfer of diverse polysaccharides to a carrier protein, allowing for methods to purify the bioconjugate from bacteria wherein it is expressed. Bioconjugation has been used successfully to produce conjugate polysaccharide for an *E. coli* four-valent O-antigen candidate vaccine (Poolman and Wacker, J. Infect. Dis. (2016) v. 213(1), pp. 6-13; WO 2015/124769; WO 2017/035181). A composition comprising 10 bioconjugates (O1A, O2, O4, O6A, O8, O15, O16, O18A, O25B and O75, the composition being referred to as ExPEC10V) has been described and is in clinical trials (e.g., WO2020/191082A1). Each of the bioconjugates are produced by a separate production strain, which show O-serotype dependent yield variation. For O-antigen production strains of several O-serotypes, yield improvements could be obtained by expressing variants of the *C. jejuni* glycosyl transferase PglB with modified substrate specificities (see e.g. WO 2016/107818, WO 2016/107819). However, for the O18 O-serotype, that displayed the lowest yields of bioconjugate production amongst the ten serotypes of which bioconjugates were made for the ExPEC10V composition, the use of variants of the *C. jejuni* PglB protein and the use of alternative PglB homologs did not lead to yield improvements. Additionally, further platform modifications aimed to increase O18 bioconjugation yield, were not successful in reaching this goal.

Among these modifications were the overexpression of WecA, a protein that initiates O-unit biosynthesis by catalyzing the transfer of N-acetylglucosamine (GlcNAc)-1-phosphate onto undecaprenyl phosphate (Und-P) to form Und-P-P-GlcNAc. Additionally, the replacement the native Wzz O-antigen chain length regulator present in the *E. coli* K-12 bioconjugation platform strain for the O-antigen chain length regulator of other gram-negative bacterial species, leading to increased O18A O-antigen chain lengths, did not result in a significantly increased product yield.

Example 1: O18 Bioconjugate Production Strain with Improved Yield

We did however obtain strains that had increased O18 bioconjugate product yields, and found that the Wzy O-antigen polymerase in those strains had amino acid mutations as compared to Wzy in the existing O18 bioconjugate production strain (that had a Wzy O-antigen polymerase having SEQ ID NO: 1). Based on this, we created a novel production strain for O18 bioconjugates, which is otherwise identical as except for three amino acid mutations in its Wzy O-antigen polymerase compared to the previously described (see WO 2020/191082) O18 bioconjugate production strain. In particular, the Wzy O-antigen polymerase in the previously described strain had amino acids threonine (T), methionine (M), and valine (V) at positions 199, 377, and 395, respectively (i.e., the Wzy O-antigen polymerase of that previously described strain is given in SEQ ID NO: 1), while the new production strain had amino acids isoleucine (I), lysine (K), and alanine (A) at those respective positions.

The yield of the O18 bioconjugate in the filtered periplasmic fraction of a 200L bioreactor run after osmotic shock (i.e. at an early point in the process where a reasonable quantification of yield is possible) was about 2.4 times higher for the new strain versus the previously described strain.

The occupancy of glycosylation sites of an EPA carrier protein that had four N-glycosylation consensus sequences was increased in the new strain versus the previously described strain, i.e. the new strain induced more di-, tri-, and tetra-glycosylated EPA carrier protein (e.g. FIG. 1).

Example 2: Construction of Modified Wzy O-Antigen Polymerases

Next we undertook a mutagenesis study of the Wzy O-antigen polymerase amino acid sequence and we identified specific combinations of amino acid substitutions in these three positions in the Wzy O-antigen polymerase sequence of SEQ ID NO: 1 that had an effect on yield and glycosylation pattern of the O18 bioconjugates.

Various combinations of amino acid substitutions in one or more of the positions 199, 377 and 395 in the amino acid sequence of SEQ ID NO: 1 of the Wzy O-antigen polymerase were produced using site directed mutagenesis using standard procedures. The various combinations that were generated are indicated in Table 3.

Example 3: Production of O-Antigen Polysaccharide Using the Modified Wzy O-Antigen Polymerase The wzy gene present in the rfb cluster from *E. coli* serotype O18A (example provided as SEQ ID NO: 5) that had been inserted into the chromosome of *E. coli* K-12 bioconjugate production strain W3110, was replaced by gene variants coding for modified Wzy O-antigen polymerases having SEQ ID NO: 1 with the mutations as indicated in Table 3, by homologous recombination-based genetic modification techniques. In addition to the rfb cluster from *E. coli* serotype O18A, the *E. coli* bioconjugate production strain W3110 further comprised nucleic acid encoding EPA carrier protein (having SEQ ID NO: 3), and nucleic acid encoding the oligosaccharyl transferase PglB (having SEQ ID NO: 6). O18A polysaccharide bioconjugates were produced in shake flask cultures and extracted using osmotic shock, as previously described e.g. in WO 2020/191082.

Example 4: Characterization O18-Bioconjugates

Periplasmic extracts from shake flask cultures of *E. coli* K-12 bioconjugate production strain W3110 containing Wzy variants (with mutations as indicated in Table 3) that were induced for O18A polysaccharide bioconjugate expression, were subjected to a capillary electrophoresis immunoassay using O18A specific monoclonal antibodies for immunodetection of bioconjugates. Relative quantitation was performed for each sample based on signal intensity of the peaks corresponding to sEPA, monoglycosylated EPA and higher forms of glycosylated EPA (di-/tri-/tetra-glycosylated EPA) as determined by MW relative to the total product signal (Table 3).

TABLE 3

Wild-type and variant Wzy O antigen polymerases with amino acid substitutions in one or more of positions 199, 377 and 395 of SEQ ID NO: 1 as indicated and their effect on glycosylation pattern of the O18 bioconjugates. Variants leading to improved glycosylation pattern are indicated in bold.

| Construct ID | Wzy amino acid position | | | Percentage of each subform within total product | | |
|---|---|---|---|---|---|---|
| | 199 | 377 | 395 | sEPA | Mono | Di/Tri/Tetra |
| Previously described production strain (Wzy having SEQ ID NO: 1) | T | M | V | 31% | 45% | 24% |
| New production strain | I | K | A | 10% | 34% | 57% |
| Variant 1 | I | M | V | 26% | 45% | 29% |
| Variant 2 | T | K | V | 6% | 24% | 71% |
| Variant 3 | T | M | A | 21% | 41% | 38% |
| Variant 4 | T | K | A | 8% | 27% | 65% |
| Variant 5 | I | K | V | 10% | 30% | 61% |
| Variant 6 | I | M | A | 6% | 34% | 60% |

Example 5: Production O18 Bioconjugate with New Production Strain, and of ExPEC9V and ExPEC10V Multivalent Products that have Immunogenic Activity The new strain for production of O18A bioconjugates was used to produce O18A bioconjugate, O18A bioconjugate was extracted from the periplasm after osmotic shock, subjected to chromatography to remove host cell proteins, and the extracted bioconjugate was used to prepare a pharmaceutical composition comprising this O18A bioconjugate as a drug substance, essentially as described in WO 2020/191082 (example 8 therein).

The new O18A drug substance was also mixed with drug substances of other bioconjugates of *E. coli* O-antigens O1A, O2, O4(glc+), O6A, O15, O16, O25B, and O75, and in some cases also including O8, to obtain multivalent (9-valent, respectively 10-valent) drug products. These drug products when administered to rabbits induced antibodies against the *E. coli* serotypes of which O-antigens were present in the compositions. Thus, the bioconjugates and compositions (obtained) according to (methods of) the invention were demonstrated to be suitable to induce immune responses against *E. coli*.

The invention claimed is:

1. A gram-negative bacterial host cell comprising:
   (a) a carrier protein comprising at least one glycosylation consensus sequence;
   (b) an *E. coli* O18 rfb locus; and,
   (c) an oligosaccharyltransferase;
   wherein the cell comprises a polypeptide having Wzy O-antigen polymerase activity, which polypeptide comprises an amino acid sequence with at least 95% identity with SEQ ID NO: 1, wherein the amino acid sequence comprises:
   i) isoleucine at a position that corresponds to position 199 in SEQ ID NO: 1, lysine at a position that corresponds to position 377 in SEQ ID NO: 1, and alanine at a position that corresponds to position 395 in SEQ ID NO: 1;
   ii) threonine at a position that corresponds to position 199 in SEQ ID NO: 1, lysine at a position that corresponds to position 377 in SEQ ID NO: 1, and valine at a position that corresponds to position 395 in SEQ ID NO: 1;
   iii) threonine at a position that corresponds to position 199 in SEQ ID NO: 1, lysine at a position that corresponds to position 377 in SEQ ID NO: 1, and alanine at a position that corresponds to position 395 in SEQ ID NO: 1;
   iv) isoleucine at a position that corresponds to position 199 in SEQ ID NO: 1, lysine at a position that corresponds to position 377 in SEQ ID NO: 1, and valine at a position that corresponds to position 395 in SEQ ID NO: 1; or
   v) isoleucine at a position that corresponds to position 199 in SEQ ID NO: 1, methionine at a position that corresponds to position 377 in SEQ ID NO: 1, and alanine at a position that corresponds to position 395 in SEQ ID NO: 1.

2. A host cell according to claim 1, wherein the polypeptide having Wzy O-antigen polymerase activity comprises the amino acid sequence of SEQ ID NO: 1, except that the amino acid sequence comprises:
   i) isoleucine at a position that corresponds to position 199 in SEQ ID NO: 1, lysine at a position that corresponds to position 377 in SEQ ID NO: 1, and alanine at a position that corresponds to position 395 in SEQ ID NO: 1;
   ii) threonine at a position that corresponds to position 199 in SEQ ID NO: 1, lysine at a position that corresponds to position 377 in SEQ ID NO: 1, and valine at a position that corresponds to position 395 in SEQ ID NO: 1;
   iii) threonine at a position that corresponds to position 199 in SEQ ID NO: 1, lysine at a position that corresponds to position 377 in SEQ ID NO: 1, and alanine at a position that corresponds to position 395 in SEQ ID NO: 1;
   iv) isoleucine at a position that corresponds to position 199 in SEQ ID NO: 1, lysine at a position that corresponds to position 377 in SEQ ID NO: 1, and valine at a position that corresponds to position 395 in SEQ ID NO: 1; or
   v) isoleucine at a position that corresponds to position 199 in SEQ ID NO: 1, methionine at a position that corresponds to position 377 in SEQ ID NO: 1, and alanine at a position that corresponds to position 395 in SEQ ID NO: 1.

3. A host cell according to claim 1, wherein the polypeptide having Wzy O-antigen polymerase activity comprises isoleucine at a position that corresponds to position 199 in SEQ ID NO: 1, lysine at a position that corresponds to position 377 in SEQ ID NO: 1, and alanine at a position that corresponds to position 395 in SEQ ID NO: 1.

4. A host cell according to claim 1, wherein a polynucleotide or vector encoding the polypeptide having Wzy O-antigen polymerase activity is integrated into the genome of the host cell.

5. A host cell according to claim 1, wherein the host cell is an *Escherichia coli* host cell.

6. A host cell according to claim 5, wherein the host cell is an *E. coli* K-12 strain.

7. A host cell according to claim 1, wherein at least one of:
   a) the oligosaccharyl transferase comprises an amino acid sequence with at least 95% sequence identity to SEQ ID NO: 6;
   b) the carrier protein comprises SEQ. ID NO. 3; and,
   c) the *E. coli* O18 rfb locus is an rfb locus of an *E. coli* strain having serotype O18A.

8. A host cell according to claim 1, wherein the oligosaccharyl transferase comprises the amino acid sequence of SEQ ID NO: 6.

9. A host cell according to claim 1, wherein the host cell comprises an *E. coli* O18 rfb locus with a nucleotide sequence encoding a Wzy O-antigen polymerase that encodes a polypeptide having Wzy O-antigen polymerase activity and having a sequence as defined in claim 1.

10. A method for producing a bioconjugate of an *E. coli* O18 antigen polysaccharide conjugated to a carrier protein, the method comprising: culturing a host cell according to any claim 1 to produce the bioconjugate.

11. A method according to claim 10, further comprising recovery of the bioconjugate.

12. A method according to claim 11, further comprising formulating the recovered bioconjugate into a pharmaceutical composition.

13. A method according to claim 12, further comprising adding one or more additional bioconjugates of *E. coli* O-antigen polysaccharides conjugated to a carrier protein to the pharmaceutical composition to obtain a multivalent bioconjugate composition.

14. A method according to claim 13, wherein the one or more additional bioconjugates comprise at least one O-antigen polysaccharide selected from the group consisting of *E. coli* serotypes O1, O2, O4, O6, O8, O15, O16, O25 and O75.

15. A method according to claim 14, wherein the multivalent bioconjugate composition comprises:
- (i) the bioconjugate of an *E. coli* O18A antigen polysaccharide conjugated to a carrier protein;
- (ii) a bioconjugate of an *E. coli* O1A antigen polysaccharide conjugated to a carrier protein;
- (iii) a bioconjugate of an *E. coli* O2 antigen polysaccharide conjugated to a carrier protein;
- (iv) a bioconjugate of an *E. coli* glucosylated O4 antigen polysaccharide conjugated to a carrier protein;
- (v) a bioconjugate of an *E. coli* O6A antigen polysaccharide conjugated to a carrier protein;
- (vi) a bioconjugate of an *E. coli* O15 antigen polysaccharide conjugated to a carrier protein;
- (vii) a bioconjugate of an *E. coli* O16 antigen polysaccharide conjugated to a carrier protein;
- (viii) a bioconjugate of an *E. coli* O25B antigen polysaccharide conjugated to a carrier protein; and,
- (ix) a bioconjugate of an *E. coli* O75 antigen polysaccharide conjugated to a carrier protein.

16. A method according to claim 15, wherein the multivalent bioconjugate composition further comprises:
- (x) a bioconjugate of an *E. coli* O8 antigen polysaccharide conjugated to a carrier protein.

17. The method of claim 15, wherein the carrier protein in each bioconjugate comprises SEQ ID NO: 3.

18. The method of claim 16, wherein the carrier protein in each bioconjugate comprises SEQ ID NO: 3.

19. The host cell according to claim 6, wherein the *E. coli* K-12 strain is W3110.

* * * * *

SEQUENCE LISTING

<160> NUMBER OF SEQ ID NOS: 6

<210> SEQ ID NO 1
<211> LENGTH: 396
<212> TYPE: PRT
<213> ORGANISM: Escherichia coli

```
<400> SEQUENCE: 1

Met Ile Tyr Ile Leu Thr Leu Thr Leu Leu Val Ile Ala Ile Met
1               5                   10                  15

Phe Ser Leu Leu Gly Thr Lys Ser Arg Ile Thr Ser Pro Leu Pro Leu
            20                  25                  30

His Phe Leu Pro Trp Leu Leu Thr Leu Ile Val Gly Ile Ser Asn Tyr
            35                  40                  45

Asp Gln Phe Tyr Glu Phe Asn Glu Arg Ser Phe Tyr Ser Leu Leu Ile
    50                  55                  60

Trp Phe Thr Val Ile Phe Ile Phe Tyr Phe Ile Gly Glu Leu Val Asn
65                  70                  75                  80

Tyr Lys Arg Glu Asn Ile Asn Val Tyr Tyr Gly Leu Ser His Ile Lys
                85                  90                  95

Tyr Glu Cys Lys Lys Tyr Trp Ile Ile Val Ile Pro Ile Ser Leu Tyr
            100                 105                 110

Thr Ile Phe Glu Ile Tyr Met Val Gly Met Gly Gly Ala Asp Gly Phe
            115                 120                 125

Phe Leu Asn Leu Arg Leu Ala Asn Thr Leu Glu Gly Tyr Thr Gly Lys
    130                 135                 140

Lys Phe Ile Leu Met Pro Ala Val Tyr Pro Leu Met Met Ala Met Phe
145                 150                 155                 160

Ala Ile Val Cys Leu Thr Lys Thr Ser Lys Leu Asn Lys Tyr Ser Ile
                165                 170                 175

Tyr Phe Trp Met Phe Leu Tyr Cys Ile Gly Thr Met Gly Lys Phe Ser
            180                 185                 190

Ile Leu Thr Pro Ile Leu Thr Tyr Leu Ile Ile Tyr Asp Phe Lys His
            195                 200                 205

Arg Leu Lys Val Lys Lys Thr Ile Lys Phe Thr Leu Leu Ile Ile Ile
    210                 215                 220

Leu Ala Leu Thr Leu His Phe Thr Arg Met Ala Glu Asn Asp His Ser
225                 230                 235                 240

Thr Phe Leu Ser Ile Leu Gly Leu Tyr Ile Tyr Ser Pro Ile Ile Ala
                245                 250                 255

Leu Gly Gln Leu Asn Glu Val Asn Ser Ser His Phe Gly Glu Tyr Thr
            260                 265                 270

Phe Arg Phe Ile Tyr Ala Ile Thr Asn Lys Ile Gly Leu Ile Lys Glu
            275                 280                 285

Leu Pro Val Asn Thr Ile Leu Asp Tyr Ser Tyr Val Pro Val Pro Thr
    290                 295                 300

Asn Val Tyr Thr Ala Leu Gln Pro Phe Tyr Gln Asp Phe Gly Tyr Thr
305                 310                 315                 320

Gly Ile Ile Phe Gly Ala Val Leu Tyr Gly Leu Ile Tyr Val Ser Leu
                325                 330                 335

Tyr Thr Ala Gly Val Arg Gly Asn Asn Thr Gln Ala Leu Leu Ile Tyr
            340                 345                 350

Ala Leu Phe Ser Val Ser Ser Ala Thr Ala Phe Phe Ala Glu Thr Leu
    355                 360                 365

Val Thr Asn Leu Ala Gly Asn Val Met Leu Val Leu Cys Thr Ile Leu
370                 375                 380

Leu Trp Arg Phe Thr Val Ile Cys Lys Pro Val Gln
385                 390                 395

<210> SEQ ID NO 2
```

<211> LENGTH: 1191
<212> TYPE: DNA
<213> ORGANISM: Escherichia coli

<400> SEQUENCE: 2

```
atgatatata tattaacttt aactcttctt ctagttatag ccataatgtt ttctcttctc     60
ggcacaaaaa gtaggatcac atctccatta cctttgcatt ttttaccatg gttactaact    120
ttaattgtcg ggataagtaa ttacgatcaa ttttacgagt ttaatgaaag aagcttttac    180
tctttgttga tttggtttac agttattttt atattttatt tcatagggga actggttaat    240
tataaacgtg aaaatataaa tgtttattat ggtctttcac atattaaata tgaatgtaaa    300
aaatattgga tcattgtcat cccaatttca ttatatacca ttttcgaaat atatatggtt    360
ggtatggggg gagcagatgg attctttctc aatttacgtc ttgcaaatac attggagggc    420
tatacgggta aaaaatttat cttaatgcct gctgtatatc ctctaatgat ggctatgttc    480
gcaattgttt gtctaacaaa aacttccaaa ttaaataaat actccattta tttctggatg    540
tttttgtatt gtattggcac aatgggaaaa ttttcaatat taacgccaat attgacatat    600
ttaattattt atgacttcaa acatagatta aaagtaaaaa aaacaataaa gtttacattg    660
ttgataatta tattagcttt aactttgcat tttacacgta tggctgagaa tgaccactca    720
acatttttat ctattttagg gctctatatt tattcaccaa taattgcttt aggccagttg    780
aatgaagtaa atagtagtca ttttggtgag tatacgttta gattcatata tgctataact    840
aataaaattg gccttattaa agaattgcca gtaaatacta ttcttgacta ttcatacgtt    900
cctgtaccaa caaatgtata tactgcactt caaccatttt accaggattt tggttatact    960
ggcatcatat ttggagcagt attatacgga ctaatatatg tgagtttata cacggccggt   1020
gttcgtggaa ataatacaca ggcattactg atttacgcat tgttttcagt tagcagtgca   1080
acggctttct tcgctgaaac gctagtaacg aatttagctg gaaatgtgat gttagtatta   1140
tgtaccatct tactatggcg atttacagta atatgcaaac cagtacagta a            1191
```

<210> SEQ ID NO 3
<211> LENGTH: 652
<212> TYPE: PRT
<213> ORGANISM: Artificial Sequence
<220> FEATURE:
<223> OTHER INFORMATION: Detoxified EPA protein comprising 4 optimized
      N-glycosylation sequences

<400> SEQUENCE: 3

```
Gly Ser Gly Gly Gly Asp Gln Asn Ala Thr Gly Ser Gly Gly Gly Lys
1               5                   10                  15

Leu Ala Glu Glu Ala Phe Asp Leu Trp Asn Glu Cys Ala Lys Ala Cys
            20                  25                  30

Val Leu Asp Leu Lys Asp Gly Val Arg Ser Ser Arg Met Ser Val Asp
        35                  40                  45

Pro Ala Ile Ala Asp Thr Asn Gly Gln Gly Val Leu His Tyr Ser Met
    50                  55                  60

Val Leu Glu Gly Gly Asn Asp Ala Leu Lys Leu Ala Ile Asp Asn Ala
65                  70                  75                  80

Leu Ser Ile Thr Ser Asp Gly Leu Thr Ile Arg Leu Glu Gly Gly Val
                85                  90                  95

Glu Pro Asn Lys Pro Val Arg Tyr Ser Tyr Thr Arg Gln Ala Arg Gly
            100                 105                 110

Ser Trp Ser Leu Asn Trp Leu Val Pro Ile Gly His Glu Lys Pro Ser
```

```
            115                 120                 125
Asn Ile Lys Val Phe Ile His Glu Leu Asn Ala Gly Asn Gln Leu Ser
130                 135                 140

His Met Ser Pro Ile Tyr Thr Ile Glu Met Gly Asp Glu Leu Leu Ala
145                 150                 155                 160

Lys Leu Ala Arg Asp Ala Thr Phe Phe Val Arg Ala His Glu Ser Asn
                165                 170                 175

Glu Met Gln Pro Thr Leu Ala Ile Ser His Ala Gly Val Ser Val Val
            180                 185                 190

Met Ala Gln Ala Gln Pro Arg Arg Glu Lys Arg Trp Ser Glu Trp Ala
                195                 200                 205

Ser Gly Lys Val Leu Cys Leu Leu Asp Pro Leu Asp Gly Val Tyr Asn
210                 215                 220

Tyr Leu Ala Gln Gln Arg Cys Asn Leu Asp Asp Thr Trp Glu Gly Lys
225                 230                 235                 240

Ile Tyr Arg Val Leu Ala Gly Asn Pro Ala Lys His Asp Leu Asp Ile
                245                 250                 255

Lys Asp Asn Asn Ser Thr Pro Thr Val Ile Ser His Arg Leu His
            260                 265                 270

Phe Pro Glu Gly Gly Ser Leu Ala Ala Leu Thr Ala His Gln Ala Cys
                275                 280                 285

His Leu Pro Leu Glu Ala Phe Thr Arg His Arg Gln Pro Arg Gly Trp
            290                 295                 300

Glu Gln Leu Glu Gln Cys Gly Tyr Pro Val Gln Arg Leu Val Ala Leu
305                 310                 315                 320

Tyr Leu Ala Ala Arg Leu Ser Trp Asn Gln Val Asp Gln Val Ile Arg
                325                 330                 335

Asn Ala Leu Ala Ser Pro Gly Ser Gly Gly Asp Leu Gly Glu Ala Ile
            340                 345                 350

Arg Glu Gln Pro Glu Gln Ala Arg Leu Ala Leu Thr Leu Ala Ala Ala
                355                 360                 365

Glu Ser Glu Arg Phe Val Arg Gln Gly Thr Gly Asn Asp Glu Ala Gly
            370                 375                 380

Ala Ala Ser Ala Asp Val Val Ser Leu Thr Cys Pro Val Ala Lys Asp
385                 390                 395                 400

Gln Asn Arg Thr Lys Gly Glu Cys Ala Gly Pro Ala Asp Ser Gly Asp
                405                 410                 415

Ala Leu Leu Glu Arg Asn Tyr Pro Thr Gly Ala Glu Phe Leu Gly Asp
                420                 425                 430

Gly Gly Asp Val Ser Phe Ser Thr Arg Gly Thr Gln Asn Trp Thr Val
            435                 440                 445

Glu Arg Leu Leu Gln Ala His Arg Gln Leu Glu Glu Arg Gly Tyr Val
            450                 455                 460

Phe Val Gly Tyr His Gly Thr Phe Leu Glu Ala Ala Gln Ser Ile Val
465                 470                 475                 480

Phe Gly Gly Val Arg Ala Arg Ser Gln Asp Leu Asp Ala Ile Trp Arg
                485                 490                 495

Gly Phe Tyr Ile Ala Gly Asp Pro Ala Leu Ala Tyr Gly Tyr Ala Gln
            500                 505                 510

Asp Gln Glu Pro Asp Ala Arg Gly Arg Ile Arg Asn Gly Ala Leu Leu
            515                 520                 525

Arg Val Tyr Val Pro Arg Trp Ser Leu Pro Gly Phe Tyr Arg Thr Gly
            530                 535                 540
```

```
Leu Thr Leu Ala Ala Pro Glu Ala Ala Gly Glu Val Glu Arg Leu Ile
545                 550                 555                 560

Gly His Pro Leu Pro Leu Arg Leu Asp Ala Ile Thr Gly Pro Glu Glu
                565                 570                 575

Glu Gly Gly Arg Val Thr Ile Leu Gly Trp Pro Leu Ala Glu Arg Thr
            580                 585                 590

Val Val Ile Pro Ser Ala Ile Pro Thr Asp Pro Arg Asn Val Gly Gly
        595                 600                 605

Asp Leu Asp Pro Ser Ser Ile Pro Asp Lys Glu Gln Ala Ile Ser Ala
    610                 615                 620

Leu Pro Asp Tyr Ala Ser Gln Pro Gly Lys Pro Pro Arg Glu Asp Leu
625                 630                 635                 640

Lys Leu Gly Ser Gly Gly Gly Asp Gln Asn Ala Thr
                645                 650

<210> SEQ ID NO 4
<211> LENGTH: 5
<212> TYPE: PRT
<213> ORGANISM: Artificial Sequence
<220> FEATURE:
<223> OTHER INFORMATION: Optimized N-glycosylation consensus sequence
<220> FEATURE:
<221> NAME/KEY: misc_feature
<222> LOCATION: (1)..(1)
<223> OTHER INFORMATION: Xaa can be Asp or Glu
<220> FEATURE:
<221> NAME/KEY: misc_feature
<222> LOCATION: (2)..(2)
<223> OTHER INFORMATION: Xaa can be any natural amino acid except Pro
<220> FEATURE:
<221> NAME/KEY: misc_feature
<222> LOCATION: (4)..(4)
<223> OTHER INFORMATION: Xaa can be any natural amino acid except Pro
<220> FEATURE:
<221> NAME/KEY: misc_feature
<222> LOCATION: (5)..(5)
<223> OTHER INFORMATION: Xaa can be Ser or Thr

<400> SEQUENCE: 4

Xaa Xaa Asn Xaa Xaa
1               5

<210> SEQ ID NO 5
<211> LENGTH: 13039
<212> TYPE: DNA
<213> ORGANISM: Escherichia coli

<400> SEQUENCE: 5
atgacgaatt taaaagcagt tattcctgta gcgggtcttg ggatgcatat gttgcctgcc      60
actaaggcga ttcccaaaga gatgctaccg atcgtcgaca agccaatgat tcagtacatc     120
gttgacgaga ttgtggctgc agggatcaaa gaaatcctcc tggtaactca cgcgtccaag     180
aacgcggtcg aaaaccactt cgacacctct tatgaattag aatctctcct gaacagcgc     240 gtgaagcgtc aactgctggc ggaagtacag tccatttgcc cgccgggcgt gacaattatg     300
aacgtgcgtc agggcgaacc tttaggtttg ggccactcca ttttatgtgc acgacctgcc     360
attggtgaca atccatttgt cgtggtgctg ccagacgttg tgatcgacga cgccagcgcc     420
gacccgctgc gctacaacct tgctgccatg attgcgcgct taacgaaac tggccgcagc     480 caggttctgg caaaacgcat gccgggcgat ctctctgaat actccgtcat ccagactaaa     540
gaaccgcttg atcgcgaagg taagtcagc cgcattgttg aatttatcga aaaccggat      600
```

```
cagccgcaga ccctggactc agacatcatg gctgtagggc gttatgtgct ttctgccgat    660
atttggcctg aactggagcg tactcaacct ggagcatggg gacgtattca gttgactgat    720
gccattgctg agttggcaaa aaacaagca gttgacgcaa tgctgatgac tggggacagt    780
tacgactgcg gaaagaaaat gggttatatg caagcgtttg tgaagtatgg gctgcgtaac    840
ctaaaagaag gggcgaagtt ccgtaaaggg attgagaagc tgttaagcga ataatgaaaa    900
tctgaccgga tgtaacggtt gataagaaaa ttataacggc agtgaagatt agcggcgaaa    960
gtaatttgtt gcgaattttc ctgccgttgt tttatataaa caatcagaat aacaacgagt   1020
tagcaacagg attatcgtca aagttttcca ggattttcct tgtttccaga gcggattggt   1080
aagacaatta gcttctgaat ttttcgggtt tagcgcgagt gggtaacact cgtcacatcg   1140
taggcatgca tgcagtgctc tggtagctgt aaagccaggg gcggtagcgt gcattaatac   1200
ctctattaat caaactgaga gccgcttatt tcacagcatg ctctgaagta atatggaata   1260
aattaagtga aaatacttgt tactggtggc gcaggattta ttggttctgc tgtagttcgt   1320
cacattataa atgatacgca ggatagtgtt gttaatgtcg ataaattaac gtacgccgga   1380
aacctggaat cacttgcaga tgtttctgat tctgaacgct attttcttga acatgcggat   1440
atttgtgatg cagctgcaat ggcacggatt tttgctcagc atcagccgga tgcagtgatg   1500
cacctggcag ctgaaagcca tgttgaccgt tcaattacag gccctgcggc atttattgaa   1560
accaatattg ttggtactta tgtccttttta gaagcggctc ggaattactg gtctgcactt   1620
gatggcgaca agaaaaacag cttccgtttt catcatattt ctactgacga agtctatggt   1680
gatttgcctc atcctgacga ggtaaataat aagaaggat taccccttatt tactgagacg   1740 acagcctacg caccaagcag cccttattct gcatcaaaag cgtccagcga tcatttagtc   1800
cgtgcgtgga acgtaccta tggtttaccg accattgtga ctaattgctc taacaattat   1860
ggtccttatc atttcccgga aaattgatt ccattggtta ttctgaatgc tctggaaggt   1920
aaaggattac ctatttatgg aaaaggcgat caaattcgcg actggctgta tgttaagat   1980 catgcgcgtg cgttatatac cgtcgtaacc gaaggtaaag cgggtgaaac ttataacatt   2040 ggtgacaca acgaaaagaa aaacatcgat gtagtgctca ctatttgtga tttgttggat   2100
gagattgtcc cgaaagagaa atcttaccgc gagcaaatta cttatgttgc cgatcgtccg   2160
ggacacgatc gacgttatgc gattgatgct gagaagattg gtcgcgaatt gggatggaaa   2220
ccacaggaaa cgtttgagag cgggattcgt aaaactgtgg aatggtatct gtccaataca   2280 aaatggttg ataatgtgaa aagtggtgcc tatcaatcgt ggattgaaca gaactatgag   2340
ggccgccact aatgaatatc ctccttttg gcaaaacagg gcaggttggt tgggaactac   2400
agcgtgctct ggcaccctctg ggtaatttga ttgctcttga tgttcactcc actgattact   2460
gtggtgattt tagtaaccct gaaggtgtgg ctgaaaccgt tagaagcatt cggcctgata   2520
ttattgtcaa cgcagccgct cacaccgcag tagacaaagc agaatcagaa ccggagtttg   2580
cacaattact gaacgcgacg agtgtcgaag cgatcgcgaa agcagccaat gaagtcggcg   2640
cttgggttat tcactactct actgactacg tatttccggg gaccggtgaa ataccatggc   2700
aggaggagga tgcaaccgca ccgctaaatg tttacggtga aaccaagtta gcaggagaaa   2760
aagcattaca agagcattgt gcgaagcacc ttattttccg gaccagctgg gtctatgcag   2820
gtaaaggaaa taacttcgcc aaaacgatgt tgcgtctggc aaaagagcgt gaagaattag   2880
ccgttattaa tgatcagttt ggtgcgccaa ctggcgcaga gttgctggct gattgtacgg   2940
cacatgccat tcgtgtggca ctgaataaac cggaagtcgc aggtttgtac catctggtag   3000
```

```
ccagtggtac cacaacctgg cacgattatg ctgcgctggt ttttgaagag gcgcgcaaag   3060
caggcattcc ccttgcactc aacaagctca acgcagtacc aacaacagtc tatcctacac   3120
cagctcgtcg tccacataac tctcgcctta atacagaaaa atttcagcag aactttgcgc   3180
ttgtcttgcc tgactggcag gttggtgtga aacgcatgct caacgaatta tttacgacta   3240
cagcaattta atagtttttg catcttgttc gtgatggtgg aacaagatga attaaaagga   3300
atgatggaat gaaaacgcgt aaaggtatta ttttagcggg tggttctggt acacgtcttt   3360
atcctgtgac tatggctgtc agtaaacagc tgttaccgat ttatgataaa ccgatgatct   3420 attaccgct ctctacactg atgttggcgg gtattcgcga tattttgatt atcagcacgc   3480
cacaggatac tcctcgtttt caacaactgc tgggtgatgg gagccagtgg gggctaaatc   3540
ttcactacaa agtgcaaccg agtccggatg gtcttgcgca ggcatttatc atcggtgaag   3600
agtttatcgg tggtgatgat gtgctttggg tacttggtga taatatcttc tacggtcacg   3660
acctgcctaa gttaatggat gccgctgtta acaaagaaag tggtgcaacg gtatttgcct   3720
atcacgttaa tgatcctgaa cgctatggtg tcgttgagtt tgataaaaac ggtacggcaa   3780
ttagcctcga agaaaaaccg ctacaaccaa aaagtaatta tgcagtaacc gggctttatt   3840
tctatgataa ctacgttgtg gaaatggcga aaaatcttaa gccttctgcc cgcggtgaac   3900
tggaaattac cgatattaac cgtatttata tggaacaggg gcatttatct gttgccatga   3960
tgggacgtgg ttatgcatgg ctggacacgg ggacacatca gagtcttatt gaagcaagca   4020
acttcattgc caccattgaa gagcgccagg gactaaaggt ttcctgccca gaagaaattg   4080
cttatcgtaa aggatttatt gacgcagagc aggttaaggt attagccgaa ccgctgaaga   4140
aaaacgctta tggtcagtat ttgctgaaaa tgattaaagg ttagtaataa aatgaatgtt   4200
attaaaacag aaattccaga cgtactgatt tttgaaccga agttttttgg tgacgagcgc   4260
ggtttctttt tcgaaagcta taaccagagg gttttttgagg aagctgtagg tcgcaaagtt   4320
gagtttgttc aggataacca ttctaaatcg agaaaaggag tattgcgggg attgcattat   4380
caattagagc cgtatgcgca agcaaaactt gtgcgttgca ttgagggtga agtatttgat   4440
attgctgtag atatacggaa gtcatctcca tttttttggta aatgggttgg tgtaacatta   4500
tccgctgaaa ataaacgtca attatggatc cctgaagggt ttgctcatgg tttttgtggtg   4560 attagtgata ctgcggaatt tgtctataaa acgaacaatt attacagtca acaagcagag   4620
cgaagcataa ttttttgatga taaagactta gggattgctt ggccattgaa tactcattat   4680 attcttttcag aaaaagattt aaatgcgcca acatttaaga aatatcgag taatgagtat   4740 tttaaatgag tttaatcaaa aacagttttt ggaacctttg cgggtatgta cttccagcta   4800
ttgtgacact accagctttg ggtattatgg ggcgaaaatt aggcccagaa ttatttggtg   4860
tattcacttt ggcattagct gttgtgggtt atgcaagcat ttttgatgca ggccttactc   4920
gcgcagtgat acgagaagtc gcaattgaaa aagataatga agaaaataag ttgaaaatta   4980
tttcttcagc gacagttgta attatttatt tgagtttggc cgcctcactc ttattatttt   5040
tttttagtgg tcatatcgca ttgctactga acattagtga gacttttttt cataatgtaa   5100
gtgtctcgct taaaattctc gcagcatcca taccattatt tttgattact caaatatggt   5160
tgtcaatttt agaaggtgaa gaaagatttg gtttacttaa tatctacaaa tcaattacgg   5220
gagtgatatt agcaatctca ccggcattat ttatactttat taaaccctct tgatgtatg   5280 cgataatagg cttagttcta gcaaggttttt tatgttttat ttttggcttttt ataatttgtc   5340
```

```
acgataaagt gcttaaagct aaactaacaa tcgatatacc aacaattaaa agattgttta    5400
tgttcggtgg ttggattaca gtaagtaata tcatcagccc tgtgctatca tattttgata    5460
ggtttattgt ttcaaatcaa cttggggctg ctaatgttgc ttttttatact gcaccatcag   5520 aaattatttc tcggcttagt ataattccag gtgcgttttc aagagcctta tttccaagat    5580
tagctaatgc aaataattcc gctgaaagat ataaaacgaa aagattaatt acaatttcac    5640
ttttaataat catcacccct attttttgta ttggcgtgtt attttcagag aagataatgg    5700
ttttatggat gggggcatca ttttttggtg agcctggttt ggtattatca atattactga    5760
ttggctttat ttttaatgga ttggcacaag taccatttgc cagtattcaa tcccgaggtc    5820
atgctaagat aactgcattt gttcatctct tagagttgtt tccttattta ttacttttat    5880
tttacctcat aaaagcacat ggggttgttg gcgcgggtat tgcgtggtca gtgaggatga    5940
tagtagatta tatagcatta agtcttttgg acggtaagta tattaataaa taaaattcaa    6000
aatgcaagtt aataactcat ggctttattt gggtaggtga caattataa tgatatatat    6060 attaacttta actcttcttc tagttatagc cataatgttt tctcttctcg gcacaaaaag    6120
taggatcaca tctccattac ctttgcattt tttaccatgg ttactaactt taattgtcgg    6180
gataagtaat tacgatcaat tttacgagtt taatgaaaga agcttttact ctttgttgat    6240
ttggtttaca gttattttta tattttattt cataggggaa ctggttaatt ataaacgtga    6300
aaatataaat gttattatg gtctttcaca tattaaatat gaatgtaaaa atattggat    6360 cattgtcatc ccaatttcat tatataccat tttcgaaata tatatggttg gtatgggggg   6420
agcagatgga ttcttctca atttacgtct tgcaaataca ttggagggct atacgggtaa   6480
aaaatttatc ttaatgcctg ctgtatatcc tctaatgatg gctatgttcg caattgtttg    6540
tctaacaaaa acttccaaat taaataaata ctccatttat ttctggatgt ttttgtattg    6600
tattggcaca atgggaaat tttcaatatt aacgccaata ttgacatatt taattattta    6660
tgacttcaaa catagattaa aagtaaaaaa aacaataaag tttacattgt tgataattat    6720
attagcttta actttgcatt ttacacgtat ggctgagaat gaccactcaa cattttatc    6780 tattttaggg ctctatattt attcaccaat aattgcttta ggccagttga atgaagtaaa    6840
tagtagtcat tttggtgagt atacgtttag attcatatat gctataacta ataaaattgg    6900
ccttattaaa gaattgccag taaatactat tcttgactat tcatacgttc ctgtaccaac    6960
aaatgtatat actgcacttc aaccattta ccaggatttt ggttatactg gcatcatatt    7020
tggagcagta ttatacggac taatatatgt gagtttatac acggccggtg ttcgtggaaa    7080
taatacacag gcattactga tttacgcatt gttttcagtt agcagtgcaa cggctttctt    7140
cgctgaaacg ctagtaacga atttagctgg aaatgtgatg ttagtattat gtaccatctt    7200
actatggcga tttacagtaa tatgcaaacc agtacagtaa ccattctaat ggccacctac    7260
aatggcgagg ccttcatcaa aaatcagatt ttgtcactac aacaacaaac attttctaac    7320
tggcggttat ttattcagga tgatgggtct acagacaata ctatatctat aataaaaaac    7380
ttccaaaaat ctgactccag aattcggcta gttgatgata atttgaaagg tcaaggtgca    7440
ggaaaaaatt ttttatcgct gataaagtac agcgagacag attatacaat ttattgtgac    7500
caagatgata tttggttaga aaacaaaata tttgaattag taaagtatgc aaatgaaatt    7560
aaattgaatg tatcagatgc gccttcgcta gtttatgctg atggctatgc ttatatggat    7620
ggtgagggta caatcgattt ttctgggata tctaacaatc atgctgatca attaaaggat    7680 tttcttttt ttaatggtgg ataccaagga tgttctatta tgttcaatcg tgcaatgacc    7740
```

```
aaatttcttc tgaattatcg aggatttgta tatctacatg acgatatcac aacattagct    7800
gcatacgctc ttggtaaagt ttattttctc ccgaaatacc ttatgttata tagacagcac    7860
acgaatgcgg taactggtat caaaacattc cgcaatggat tgacttctaa atttaaatca    7920
ccagtaaact atcttttatc acgaaaacat tatcaggtaa aaaaatcttt ttttgaatgt    7980
aacagctcta tcttatcaga gacgaataaa aaagtttttt tggattttat ttcattttgt    8040
gaatcaaata ataaatttac agattttttt aagttatggc gaggtgggtt tagattaaat    8100
aacagtagaa ctaaattatt attaaaattc ttaatacgga gaaaatttag cgaatgattt    8160
caatacttac acctactttt aatcggcaac atactttatc aaggctattc aattctctta    8220
tattacaaac tgataaagat tttgagtgga taataattga tgatggtagt atagatgcaa    8280
cagcggtact tgtagaagat tttagaaaaa aatgtgattt tgacttgatt tattgctatc    8340
aggaaaataa tggtaagccc atggctttaa acgctggtgt taaagcttgt agaggcgatt    8400
atatctttat tgttgacagt gatgatgcac taactcccga tgccataaaa ttaattaaag    8460
aatcaataca tgattgctta tctgagaagg aaagtttcag cggagtcggt tttagaaaag    8520
catatataaa aggggggatt attggtaatg atttaaataa ttcttcagaa catatatact    8580
atttaaatgc gactgagatt agcaatttaa taaatggtga tgttgcatat tgttttaaaa    8640
aagaaagttt ggtaaaaaat ccattccccc gtatagaaga tgaaaaattt gttccagaat    8700
tatatatttg gaataaaata actgacaagg cgaagattcg atttaacata agcaaagtta    8760
tatatctttg tgagtatctt gatgatggtc tttctaaaaa tttccataac cagcttaaaa    8820
aatacccaaa ggggtttaag atttattaca aagatcaaag aaaacgagag aaaacttata    8880
taaaaaaaac aaagatgcta attagatatt tgcaatgttg ttattatgag aaaataaaat    8940
gaaaatacta tttgtcatta caggtttagg ccttggaggt gctgagaagc aggtttgtct    9000
tttagctgat aaattaagtt taagcgggca ccatgtaaag attatttcac ttggacatat    9060
gtctaataat aaagtctttc ctagcgaaaa taatgttaat gtcattaatg taaatatgtc    9120
aaaaaacatt tctggagtta taaaaggttg tgtcagaatt agagatgtta tagctaatttt   9180 caaaccagac attgtacaca gtcatatgtt tcatgcaaac attatcacta gattgtctgt    9240
aattggaatc aaaaacagac ctggtattat atcaactgca cataataaaa atgaaggtgg    9300
gtatttcaga atgctcacat atagaataac cgattgttta agtgattgtt gtacaaatgt    9360
tagcaaagaa gcagtggatg agttttttacg gataaaagcc tttaatcccg ctaaagcaat    9420
tactatgtat aatgggatag ataccaataa atttaaattt gatttattgg caaggaggga    9480
aattcgagac ggtattaata taaaaaatga tgatatatta ttacttgctg caggtcgttt    9540
aacgttagct aaagattatc ctaatttatt gaatgcaatg actctgcttc ctgaacactt    9600
taaacttatt attattggtg atggtgaatt gcgtgacgaa attaatatgc ttataaaaaa    9660
attgcaatta tctaataggg tgtccttgtt gggagttaaa aaaatatttg ctccctattt    9720
ttctgcatgt gatatttttg ttctctcttc tcgttgggaa ggatttggat tagtcgtggc    9780
agaagctatg tcatgtgagc gaattgttgt tggcacggat tcaggggggag taagagaagt    9840 tattggtgac gatgattttc ttgtacccat atctgattca acacaacttg caagcaaaat    9900
tgaaaaattg tctttgagcc agatacgtga tcacattggt tttcggaatc gtgagcgtat    9960
tttaaaaaat ttctcaatag atactattat tatgcagtgg caagaactct atggaactat   10020
aatttgctca aaacatgaaa ggtagattta tatttggaac gtgtcttttg tttgaattta   10080
```

```
attcaatctc aattgagatt tttgtatttc aaaaatacca tcatagctaa cgatgattgg    10140
tatttatttt aagatgcttt ctataaatat attgacgttt ttaatgcgcc gaaacgattg    10200
ggctgggaac agagaagtaa aactgttttg agaatgaaga gttttttgaga tgtttatgga   10260
tattaaaaat tgatccagtg aattaattat ttataataaa tcaagattta atgttaataa    10320
atgataatct tttctgacac tcatattaat tatgagtggt acgtttggta aacggtaaac    10380
tattatatga cagctagaac aactaaagtt ttgcacttac aattactccc actcttaagt    10440
ggcgttcaaa gggtaacatt aaacgaaatt agtgcgttat atactgatta tgattataca    10500
ctagtttgct caaaaaaagg tccactaaca aaagcattgc tggaatatga tgtcgattgt    10560
cattgtatcc ccgaacttac gagagaaatt accgtaaaga atgattttaa agcattgttc    10620
aagctttata agttcataaa aaagaaaaa tttgacattg tgcatacaca ttcttcaaaa     10680
acaggtattt tggggcgagt tgctgccaaa ttagcacgtg ttggaaaggt gatccacact    10740
gtacatggtt tttcttttcc agccgcatct agtaaaaaaa gttattacct ttattttttc    10800
atggaatgga tagcaaagtt ctttacggat aagttaatcg tcttgaatgt agatgatgaa    10860
tatatagcaa taaacaaatt aaaattcaag cgggataaag ttttttttaat tcctaatgga  10920
gtagacactg ataagttttc tcctttagaa aataaaattt atagtagcac cttgaatcta    10980
gtaatggttg gtagattatc caagcaaaaa gatcctgaga cattattgct tgctgttgaa    11040
aaactgctga atgaaaatgt taatgttaag ctgacacttg taggagatgg tgaactaaaa    11100
gaacagttag aaagcaggtt caaacggcaa gatggacgta taattttttca tggatggtca   11160
gataacattg ttaatatttt aaaagttaat gatcttttta tattaccttc tctttgggag    11220
ggtatgccat tagcaatttt agaagcattg agctgtggac ttccatgtat agtcactaat    11280
attccaggta ataatagctt aatagaagat ggctataatg gttgtttgtt tgaaattaga    11340
gattgtcagt tattatctca aaaaatcatg tcatatgttg gtaagccaga actgattgca    11400
cagcaatcta ccaatgcacg atcatttatt ctgaaaaatt atggattagt taaaagaaat    11460
aataaggtca gacagctata tgataattaa atgaaaccga aaagttaaaa aagaacaggt    11520
ttttcaaagt gaaaataaaa ttacagtttt tttattgcaa tgattaacgt aacatctgca    11580
ttacattcaa gccgcacaac cccgcggtga ccacccctga caggagtaaa caatgtcaaa    11640
gcaacagatc ggcgtcgtcg gtatggcagt gatgggacgc aacctcgcgc tcaacatcga    11700
aagccgtggt tataccgtct ctattttcaa ccgttcccgt gaaaagacgg aagaagttat    11760
tgccgaaaat ccaggcaaga aactggttcc ttactatacg gtgaaagagt tcgttgaatc    11820
tcttgaaacg cctcgtcgca tcctgttaat ggttaaagca ggtgcaggca cggatgctgc    11880
tattgattcc ctgaaaccat atctcgataa aggcgatatc atcattgatg gtggtaatac    11940
cttcttccag gacaccattc gtcgtaaccg cgagctttct gcacaaggct ttaacttcat    12000
cggtacgggt gtttccggtg gtgaagaggg cgcgctgaaa ggaccttcta tcatgcctgg    12060
tgggcagaaa gaggcctatg aactggttgc tcctatcctg accaaaatcg ccgccgtggc    12120
tgaagatggt gaaccatgcg ttacctatat tggtgccgat ggcgcaggtc actatgtgaa    12180
gatggttcac aacggtattg aatacggtga tatgcaactg attgctgaag cctattctct    12240
gctgaaaggt ggtctgaatc tctctaacga agaactggca caaacctttta ccgagtggaa   12300
taacggtgaa ctgagcagtt acctgatcga catcactaaa gacatcttca ccaaaaaaga    12360
tgaagacggt aactacctgg ttgatgtgat cctggatgaa gcagcaaaca aaggtacggg    12420
taaatggacc agtcagagcg cgctggatct cggtgagcca ctgtcgctga ttactgagtc    12480
```

```
tgtgtttgca cgctacatct cttcactaaa agatcagcgc gtggctgcgt ctaaagtact   12540
gtcgggtcca caagcgcagc cagcaggcga caaagcagag ttcattgaaa aagttcgccg   12600
tgcgctttat ctgggtaaga ttgtttctta cgcgcagggc ttctctcagc tgcgtgctgc   12660
gtctgaagag tacaactggg atctgaacta cggtgaaatc gcgaagattt ccgtgctgg   12720 ctgcatcatc cgtgcgcagt tcctgcagaa aatcaccgat gcttatgccg aaaatccgca   12780
gatcgctaac ctgctgctgg ctccgtactt caagcaaatt gccgatgact accagcaggc   12840
tctgcgtgat gtcgttgctt atgcagtaca gaacggtatc ccggttccga ccttcgccgc   12900
tgcggttgcc tattacgata gctaccgtgc cgctgttctg cctgcgaacc tgatccaggc   12960
acagcgtgac tatttcggtg cacatactta taagcgcatt gataaagaag gtgtgttcca   13020
tactgaatgg ctggattga                                                13039

<210> SEQ ID NO 6
<211> LENGTH: 713
<212> TYPE: PRT
<213> ORGANISM: Artificial Sequence
<220> FEATURE:
<223> OTHER INFORMATION: PglB oligosaccharyl transferase

<400> SEQUENCE: 6

Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
                20                  25                  30

Val Trp Trp Ala Ser Glu Phe Asn Glu Tyr Phe Asn Asn Gln Leu
            35                  40                  45

Met Ile Ile Ser Asn Asp Gly Tyr Ala Phe Ala Glu Gly Ala Arg Asp
        50                  55                  60

Met Ile Ala Gly Phe His Gln Pro Asn Asp Leu Ser Tyr Tyr Gly Ser
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
                100                 105                 110

Val Ile Pro Thr Ile Leu Leu Ala Asn Glu Tyr Lys Arg Pro Leu Met
            115                 120                 125

Gly Phe Val Ala Ala Leu Leu Ala Ser Ile Ala Asn Ser Tyr Tyr Asn
        130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                165                 170                 175

Phe Phe Ser Leu Ile Ala Leu Pro Leu Phe Ile Gly Ile Tyr Leu Trp
                180                 185                 190

Trp Tyr Pro Ser Ser Tyr Thr Leu Asn Val Ala Leu Ile Gly Leu Phe
            195                 200                 205

Leu Ile Tyr Thr Leu Ile Phe His Arg Lys Glu Lys Ile Phe Tyr Ile
        210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                245                 250                 255
```

-continued

Lys Arg Leu Asn Phe Met Ile Ile Gly Ile Leu Gly Ser Ala Thr Leu
                260                 265                 270

Ile Phe Leu Ile Leu Ser Gly Gly Val Asp Pro Ile Leu Tyr Gln Leu
            275                 280                 285

Lys Phe Tyr Ile Phe Arg Ser Asp Glu Ser Ala Asn Leu Thr Gln Gly
        290                 295                 300

Phe Met Tyr Phe Asn Val Asn Gln Thr Ile Gln Glu Val Glu Asn Val
305                 310                 315                 320

Asp Leu Ser Glu Phe Met Arg Arg Ile Ser Gly Ser Glu Ile Val Phe
                325                 330                 335

Leu Phe Ser Leu Phe Gly Phe Val Trp Leu Arg Lys His Lys Ser
            340                 345                 350

Met Ile Met Ala Leu Pro Ile Leu Val Leu Gly Phe Leu Ala Leu Lys
        355                 360                 365

Gly Gly Leu Arg Phe Thr Ile Tyr Ser Val Pro Val Met Ala Leu Gly
            370                 375                 380

Phe Gly Phe Leu Leu Ser Glu Phe Lys Ala Ile Met Val Lys Lys Tyr
385                 390                 395                 400

Ser Gln Leu Thr Ser Asn Val Cys Ile Val Phe Ala Thr Ile Leu Thr
                405                 410                 415

Leu Ala Pro Val Phe Ile His Ile Tyr Asn Tyr Lys Ala Pro Thr Val
            420                 425                 430

Phe Ser Gln Asn Glu Ala Ser Leu Leu Asn Gln Leu Lys Asn Ile Ala
        435                 440                 445

Asn Arg Glu Asp Tyr Val Val Thr Trp Trp Asp Tyr Gly Tyr Pro Val
450                 455                 460

Arg Tyr Tyr Ser Asp Val Lys Thr Leu Val Asp Gly Gly Lys His Leu
465                 470                 475                 480

Gly Lys Asp Asn Phe Phe Pro Ser Phe Ala Leu Ser Lys Asp Glu Gln
                485                 490                 495

Ala Ala Ala Asn Met Ala Arg Leu Ser Val Glu Tyr Thr Glu Lys Ser
            500                 505                 510

Phe Tyr Ala Pro Gln Asn Asp Ile Leu Lys Thr Asp Ile Leu Gln Ala
        515                 520                 525

Met Met Lys Asp Tyr Asn Gln Ser Asn Val Asp Leu Phe Leu Ala Ser
530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
                565                 570                 575

Ser Phe Ser Phe Ile Asn Leu Asp Thr Gly Val Leu Asp Lys Pro Phe
            580                 585                 590

Thr Phe Ser Thr Ala Tyr Pro Leu Asp Val Lys Asn Gly Glu Ile Tyr
        595                 600                 605

Leu Ser Asn Gly Val Val Leu Ser Asp Asp Phe Arg Ser Phe Lys Ile
610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
            660                 665                 670

Leu Met Asp Lys Thr Met Phe Asn Ser Ala Tyr Val Gln Met Phe Phe

```
                675                 680                 685
Leu Gly Asn Tyr Asp Lys Asn Leu Phe Asp Leu Val Ile Asn Ser Arg
    690                 695                 700

Asp Ala Lys Val Phe Lys Leu Lys Ile
705                 710
```